(12) United States Patent
Fukuma et al.

(10) Patent No.: US 9,370,301 B2
(45) Date of Patent: Jun. 21, 2016

(54) OPHTHALMOLOGIC APPARATUS

(71) Applicant: KABUSHIKI KAISHA TOPCON, Tokyo (JP)

(72) Inventors: Yasufumi Fukuma, Tokyo (JP); Kanichi Tokuda, Tokyo (JP); Taiki Aimi, Tokyo (JP); Atsushi Kubota, Tokyo (JP); Yusuke Ono, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 13 days.

(21) Appl. No.: 14/282,730

(22) Filed: May 20, 2014

(65) Prior Publication Data

US 2014/0300864 A1    Oct. 9, 2014

Related U.S. Application Data

(63) Continuation-in-part of application No. 14/226,311, filed on Mar. 26, 2014, now Pat. No. 9,295,387.

(60) Provisional application No. 61/807,923, filed on Apr. 3, 2013.

(51) Int. Cl.
*A61B 3/14*    (2006.01)
*A61B 3/10*    (2006.01)
*A61B 3/12*    (2006.01)

(52) U.S. Cl.
CPC .. *A61B 3/102* (2013.01); *A61B 3/12* (2013.01)

(58) Field of Classification Search
USPC .......................................................... 351/206
See application file for complete search history.

(56) References Cited

U.S. PATENT DOCUMENTS

2008/0239238 A1    10/2008    Fukuma et al.

FOREIGN PATENT DOCUMENTS

| EP | 2415393 A1 | 8/2012 |
|---|---|---|
| JP | 4896794 B2 | 1/2012 |
| JP | 2013-005982 A | 1/2013 |

*Primary Examiner* — Jack Dinh
(74) *Attorney, Agent, or Firm* — Pearne & Gordon LLP

(57) ABSTRACT

An ophthalmologic apparatus of an embodiment includes an acquiring part, a first optical system, a forming part and a controller. The acquiring part acquires a first front image of an eye fundus. The first optical system scans the fundus by signal light and detects interference light of returned light of the signal light and reference light. The forming part repeatedly forms a second front image of the fundus and a cross sectional image showing a cross section perpendicular to the second front image based on the detection results repeatedly obtained by the first optical system. The controller displays the first front image on a display means, displays, as a moving image, the second front images repeatedly formed by the forming part over the first front image, and displays, as a moving image, the cross sectional images repeatedly formed by the forming part.

11 Claims, 29 Drawing Sheets

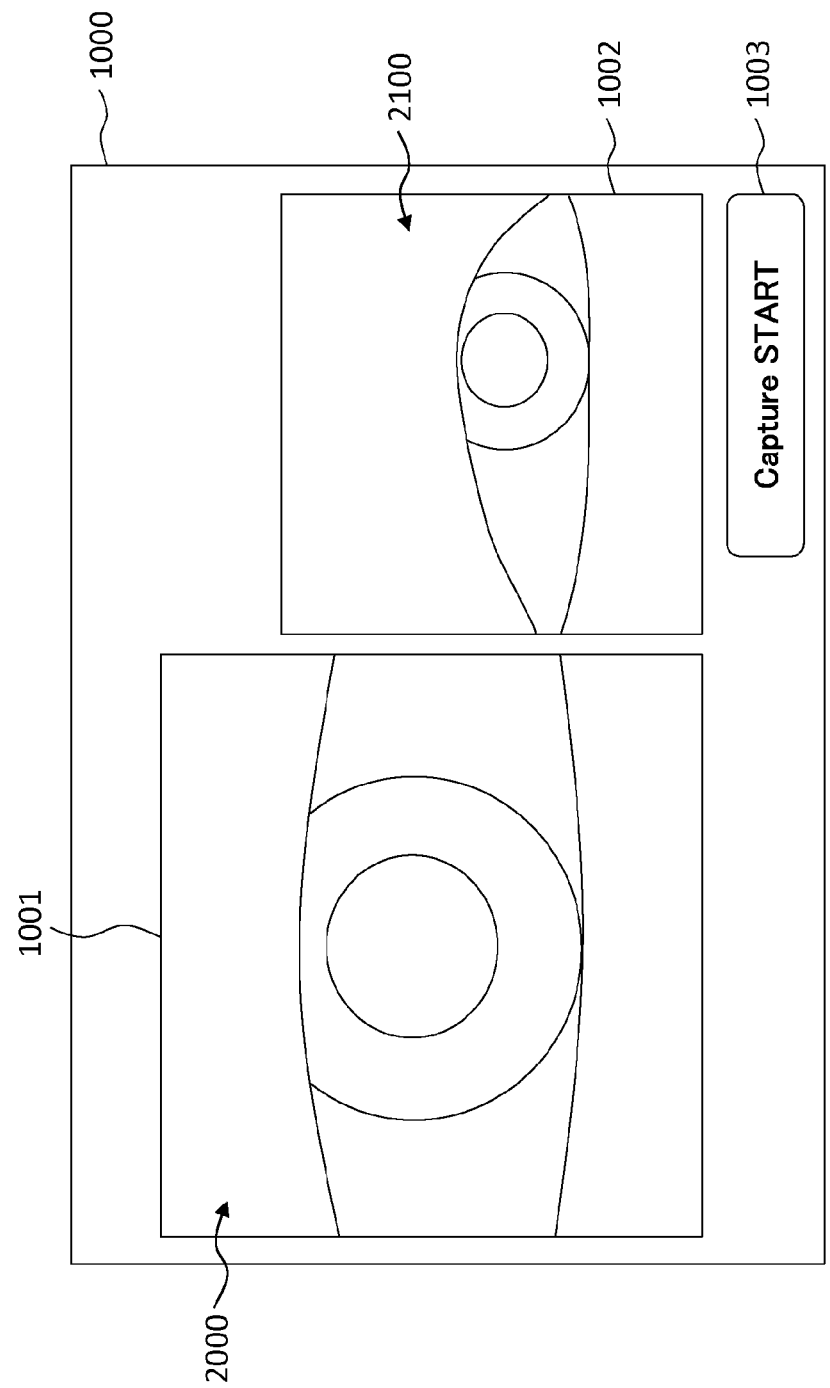

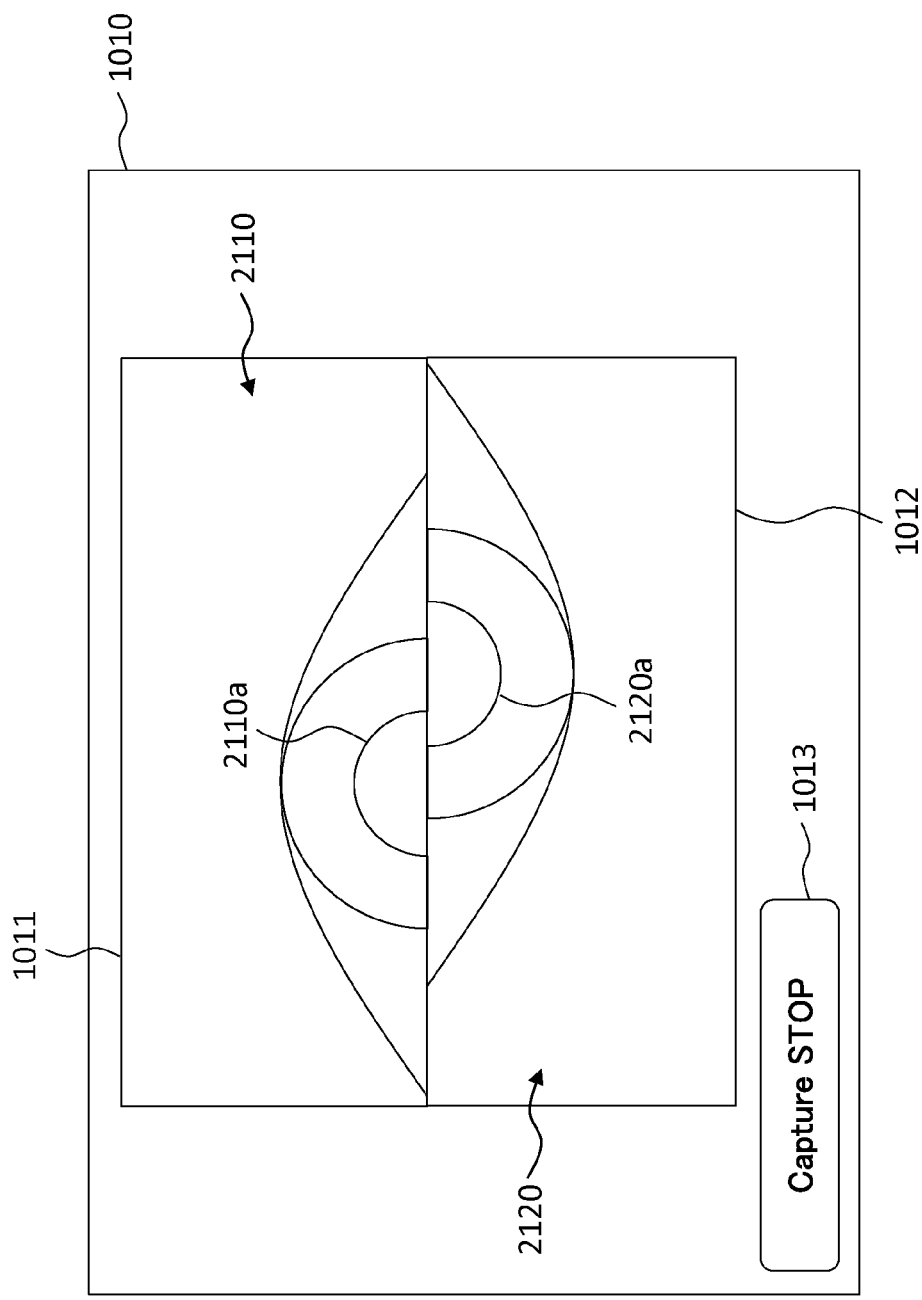

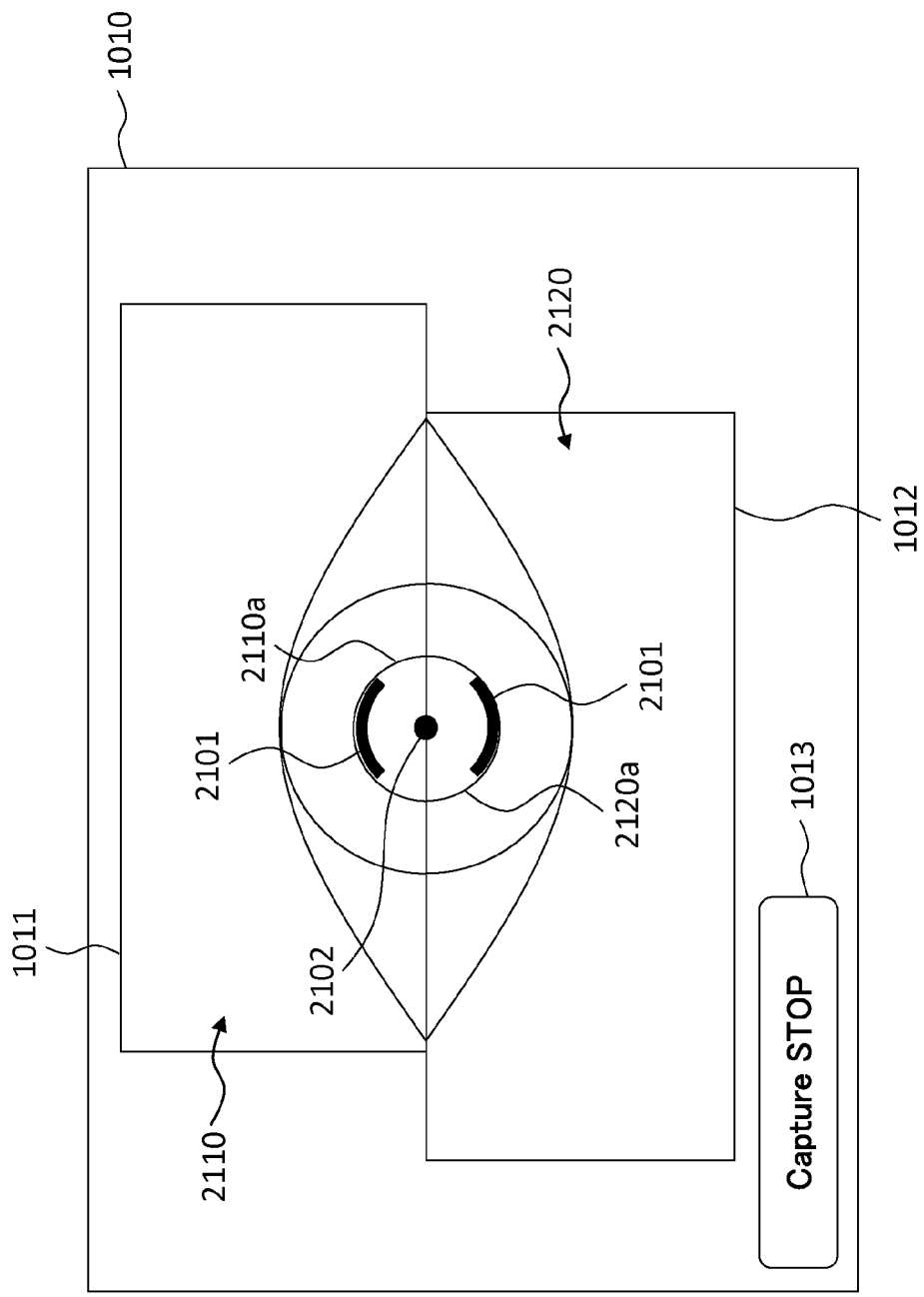

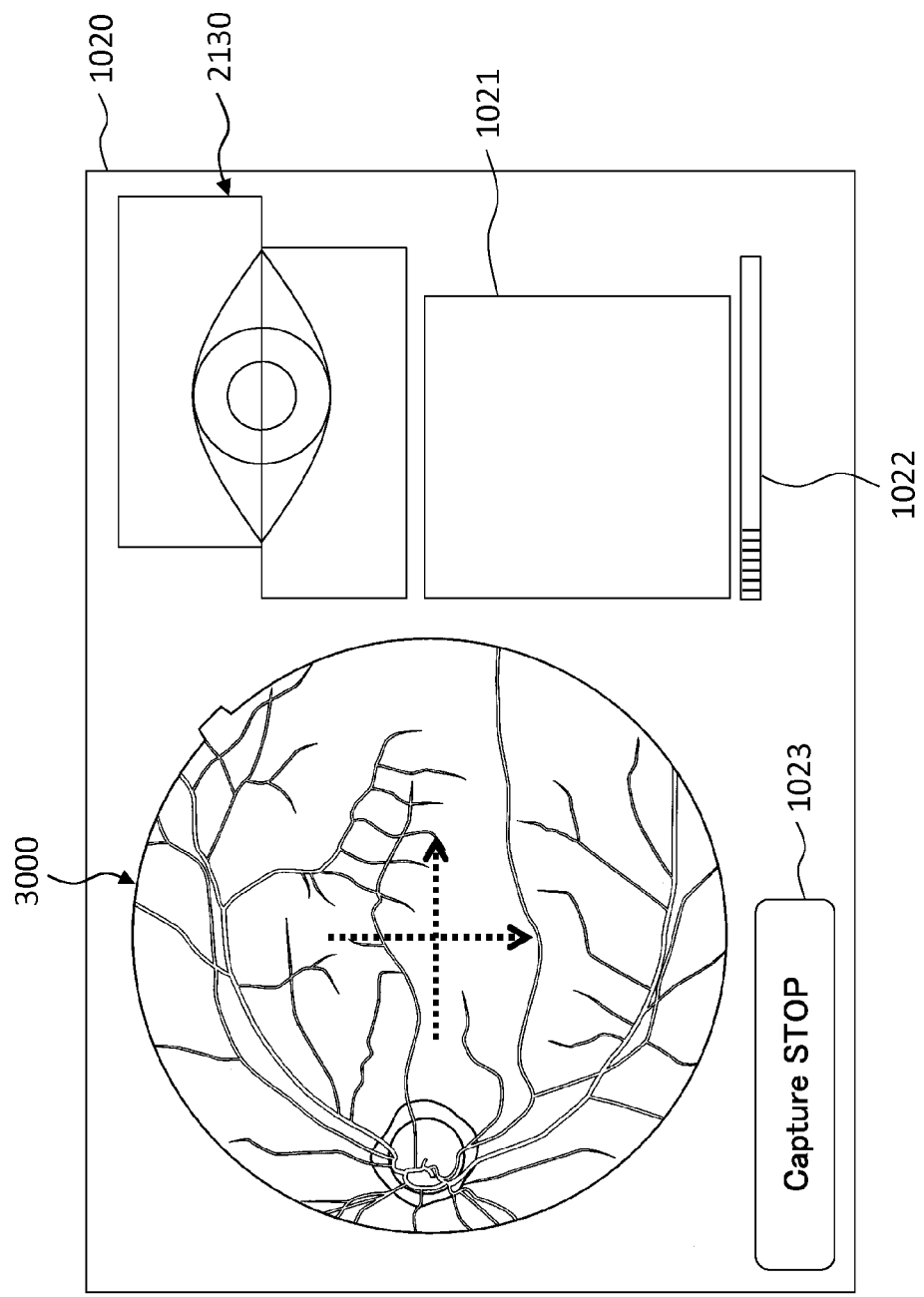

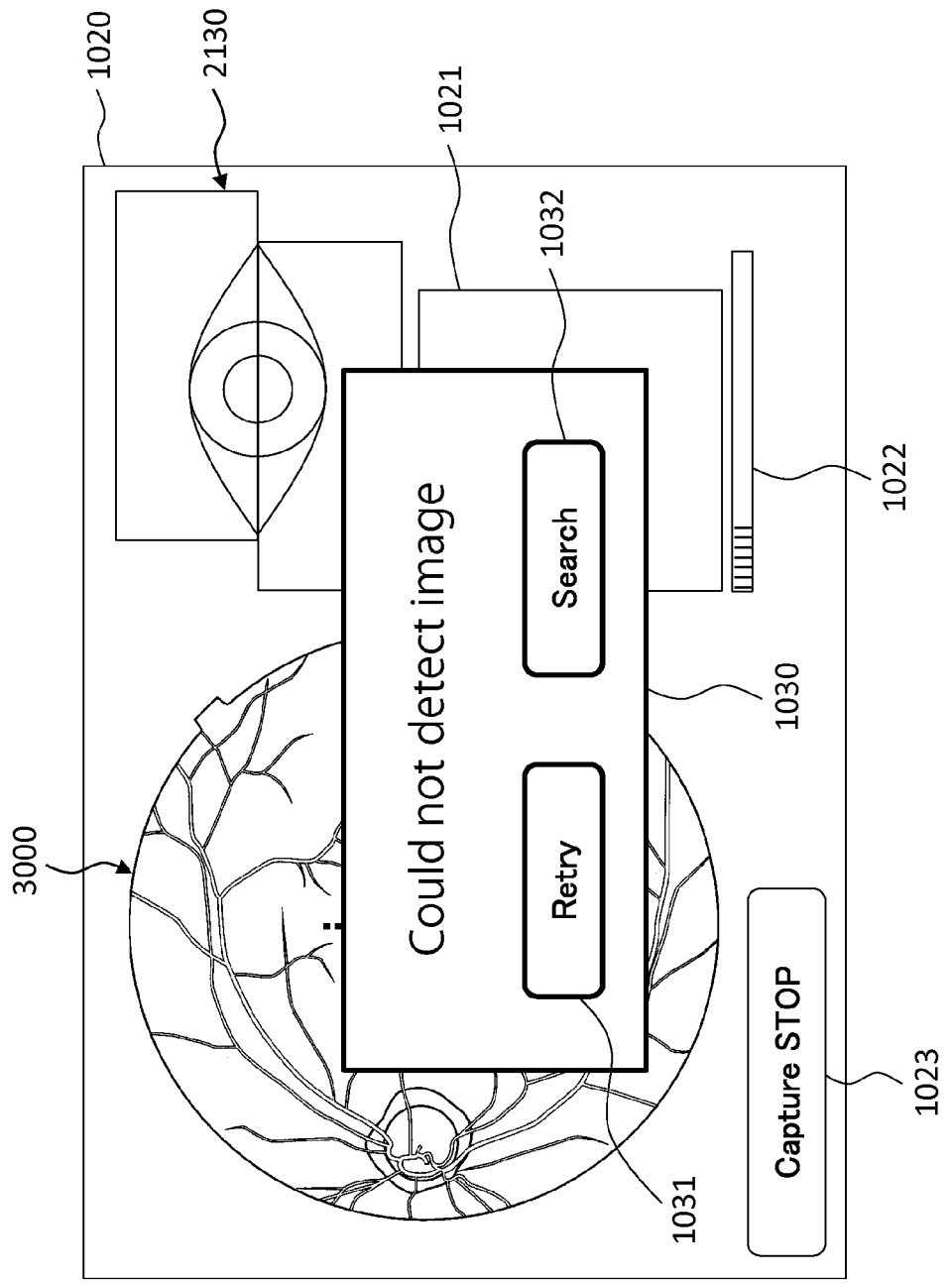

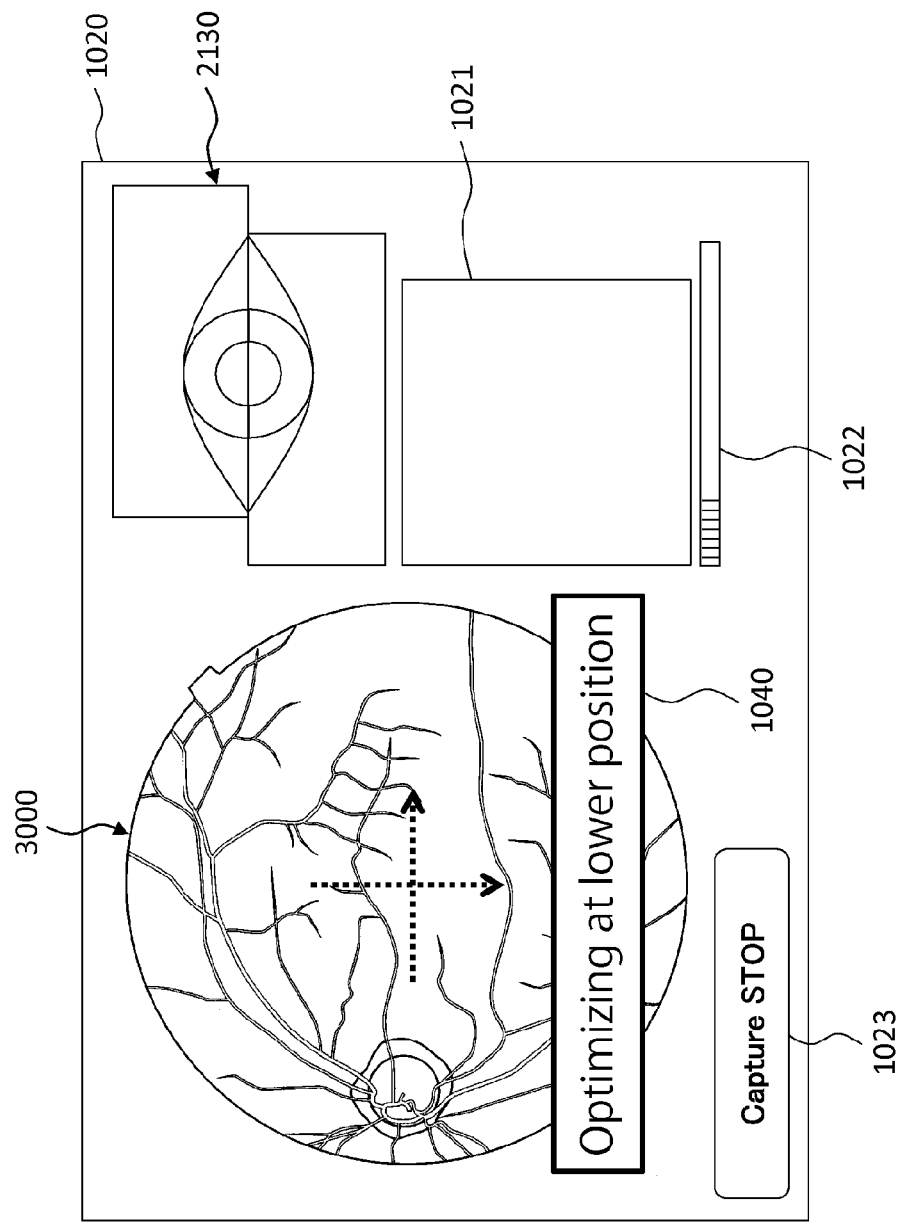

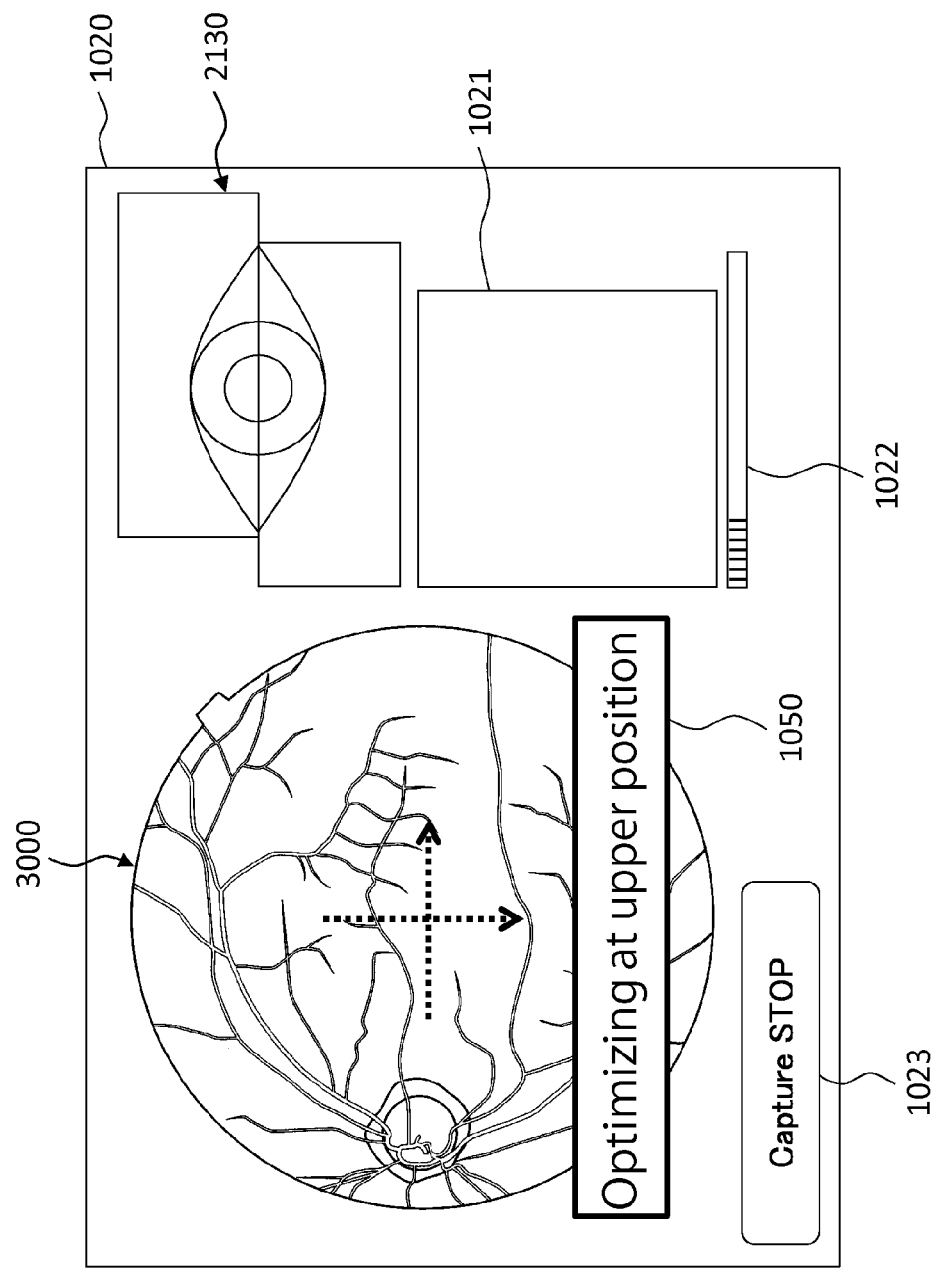

FIG. 10

| SCANNING PATTERN | SHIFTING ALIGNMENT DIRECTION |
|---|---|
| 3D Macula | INFERIOR / SUPERIOR |
| 3D Disc | |
| 3D Wide (H) | |
| 3D Macula (V) | NASAL / TEMPORAL |
| 3D Wide | |
| Radial | INFERIOR / SUPERIOR |
| 5 Line Cross | |
| Line H/V | H: INFERIOR / SUPERIOR<br>V: NASAL / TEMPORAL |

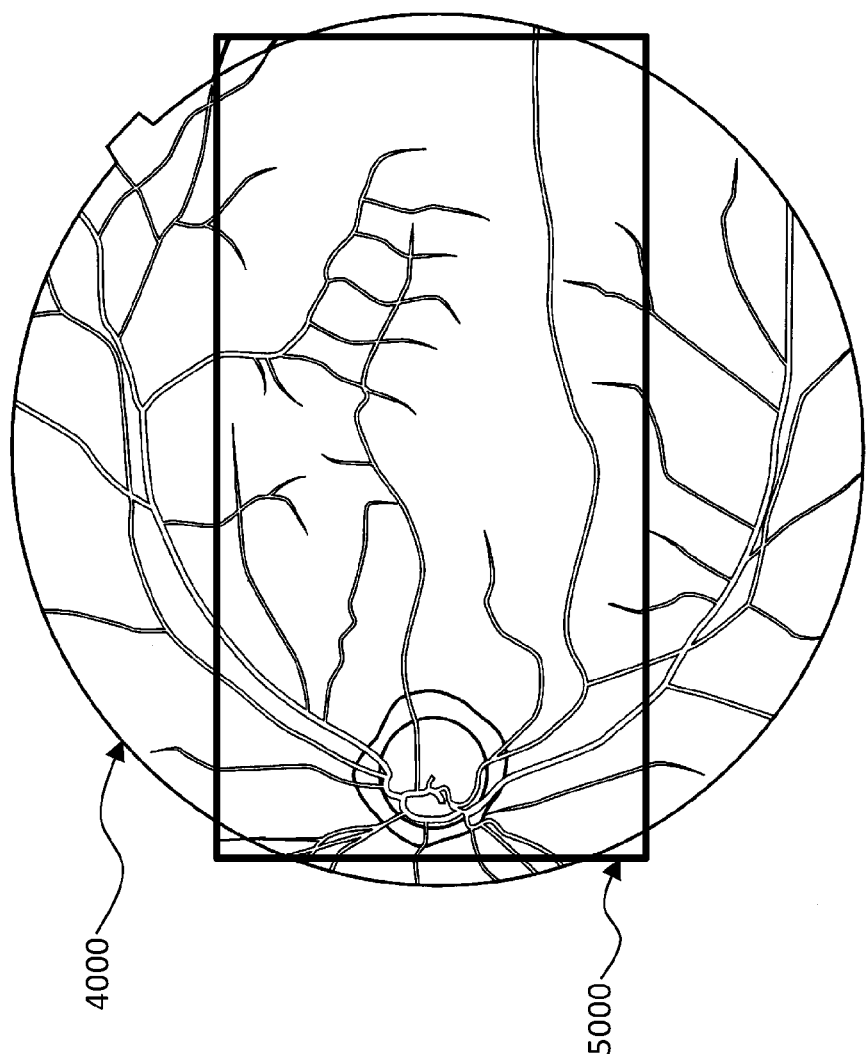

OPHTHALMOLOGIC APPARATUS

This application is a Continuation in Part of application Ser. No. 14/226,311 filed Mar. 26, 2014, which claims benefit of U.S. Provisional Application No. 61/807,923 filed Apr. 3, 2013, which are incorporated herein by reference in their entirety.

TECHNICAL FIELD

The present invention relates to an ophthalmologic apparatus that images an eye fundus by using optical coherence tomography (OCT).

BACKGROUND TECHNOLOGY

There are conventional ophthalmologic apparatuses having an OCT function that also acquires an observation image by using a retinal camera function. The observation image is a real-time moving image obtained by video filming an eye fundus from the front. This video filming generally uses near infrared light.

PRIOR ART DOCUMENT

Patent Document

[Patent Document 1] Japanese Patent No. 4896794

Problem to be Solved by the Invention

In general, for such ophthalmologic apparatuses, the minimum size of a pupil to which the retinal camera function can be applied (called the minimum pupil diameter) is larger than the minimum pupil diameter to which the OCT function can be applied. When the pupil diameter of a subject eye is less than the minimum pupil diameter for the retinal camera function, part of illumination light is blocked off by the iris, thereby decreasing the brightness of the retinal image acquired. This causes problems such as the difficulty in adjusting fixation position and in adjusting the position of OCT scanning.

It should be noted that one may administer a mydriatic agent or use a darkroom for enlarging the pupil; however, new problems appear such as a burden to the subject or prolongment of the examination.

The purpose of the present invention is to provide technology that makes it possible to preferably acquire front images of an eye fundus even though the subject eye is a microcoria (small pupil) eye.

Means for Solving the Problem

The invention of Claim 1 is an ophthalmologic apparatus comprising: an acquiring part configured to acquire a first front image of the fundus of an eye; a first optical system configured to scan the fundus by signal light and detect interference light of returned light of the signal light from the fundus and reference light; a forming part configured to repeatedly form both a second front image of the fundus and a cross sectional image showing a cross section perpendicular to the cross section shown by the second front image based on the detection results repeatedly obtained by the first optical system; and a controller configured to display the first front image on a display means, display, as a moving image, the second front images repeatedly formed by the forming part over the first front image, and display, as a moving image, the cross sectional images repeatedly formed by the forming part on the display means.

The invention of Claim 2 is the ophthalmologic apparatus of Claim 1, wherein the first optical system is configured to alternately execute a first scan mode in which the irradiation position of the signal light on the fundus is two-dimensionally changed and a second scan mode in which the irradiation position of the signal light on the fundus is one-dimensionally changed, the forming part is configured to form the second front images based on the detection results obtained by the first scan mode and form the cross sectional images based on the detection results obtained by the second scan mode, and the controller is configured to execute frame update for the movie display of the second front images and frame update for the movie display of the cross sectional images in accordance with the switching between the first and second scan modes of the first optical system.

The invention of Claim 3 is the ophthalmologic apparatus of Claim 2, further comprising a blink detecting part configured to detect the blink of the eye, wherein the controller is configured to stop the frame update in response to the fact that a blink is detected by the blink detecting part while the first optical system is executing the scan, and to resume the frame update in response to the fact that the blink is no longer detected.

The invention of Claim 4 is the ophthalmologic apparatus of Claim 2, further comprising a setting part configured to set a one-dimensional region for the second scan mode, wherein the first optical system is configured to execute the first scan mode such that a two-dimensional region in which the one-dimensional region set by the setting part is located in the center is scanned by the signal light.

The invention of Claim 5 is the ophthalmologic apparatus of Claim 2, further comprising a fixation optical system configured to project a fixation target onto the fundus based on a preset fixation position, wherein the first optical system is configured to execute the first scan mode such that a two-dimensional region having a size that is associated with the fixation position in advance is scanned by the signal light.

The invention of Claim 6 is the ophthalmologic apparatus of Claim 2, further comprising a fixation optical system configured to project a fixation target onto the fundus based on a preset fixation position, wherein the first optical system is configured to execute the first scan mode such that the irradiation position of the signal light is changed at an interval that is associated with the fixation position in advance.

The invention of Claim 7 is the ophthalmologic apparatus of Claim 2, wherein the interval of the irradiation positions of the signal light in the first scan mode and the interval of the irradiation positions of the signal light in the second scan mode are different.

The invention of Claim 8 is the ophthalmologic apparatus of Claim 1, further comprising: an information obtaining part configured to obtain information showing the pupil size of the eye; and a second optical system configured to irradiate illumination light on the fundus and repeatedly detect reflected light of the illumination light from the fundus, wherein the controller is configured to selectively execute, based on the information obtained by the information obtaining part, a first display mode in which the second front images are displayed as a movie over the first front image, and a second display mode in which a movie display is carried out based on the detection results repeatedly acquired by the second optical system.

The invention of Claim 9 is the ophthalmologic apparatus of Claim 1, wherein the acquiring part comprises a third optical system configured to irradiate illumination light on the fundus and repeatedly detect reflected light of the illumination light from the fundus, and the controller is configured to display, as the first front image, a moving image based on the detection results repeatedly acquired by the third optical system.

The invention of Claim 10 is the ophthalmologic apparatus of Claim 9, further comprising an alignment optical system configured to project a target for aligning the first optical system with the eye onto the fundus, wherein an image of the target acquired by the third optical system is displayed together with the first and second front images.

The invention of Claim 11 is the ophthalmologic apparatus of Claim 9, further comprising a focus optical system configured to project, onto the fundus, a target for carrying out focusing of the first optical system on the fundus, wherein an image of the target acquired by the third optical system is displayed together with the first and second front images.

Effect of the Invention

According to the present invention, it is possible to preferably acquire front images of an eye fundus even though the subject eye is a microcoria eye.

BRIEF EXPLANATION OF THE DRAWINGS

FIG. 8A is a schematic diagram showing an example of a screen displayed by an ophthalmologic apparatus according to an embodiment.

FIG. 8B is a schematic diagram showing an example of a screen displayed by an ophthalmologic apparatus according to an embodiment.

FIG. 8C is a schematic diagram showing an example of a screen displayed by an ophthalmologic apparatus according to an embodiment.

FIG. 8D is a schematic diagram showing an example of a screen displayed by an ophthalmologic apparatus according to an embodiment.

FIG. 8E is a schematic diagram showing an example of a screen displayed by an ophthalmologic apparatus according to an embodiment.

FIG. 8F is a schematic diagram showing an example of a screen displayed by an ophthalmologic apparatus according to an embodiment.

FIG. 8G is a schematic diagram showing an example of a screen displayed by an ophthalmologic apparatus according to an embodiment.

FIG. 10 is a schematic diagram for explaining an operational example of an ophthalmologic apparatus according to an embodiment.

FIG. 14C is a schematic diagram for explaining an operational example of an ophthalmologic apparatus according to an embodiment.

MODE FOR CARRYING OUT THE INVENTION

Embodiments of ophthalmologic apparatuses related to the present invention are explained in detail with reference to diagrams. An ophthalmologic apparatus related to the present invention has a function as optical coherence tomography (OCT). In this specification, an image obtained by optical coherence tomography is sometimes referred to as an OCT image. Furthermore, a measuring action for forming an OCT image is sometimes referred to as an OCT measurement. It should be noted that the contents of the documents cited in this specification may be employed in the following embodiments.

In the following embodiments, an OCT apparatus using OCT of so-called spectral domain type is described; however, the present invention may also be applied to OCT apparatus using other types than spectral domain, such as swept source type and en-face type. It should be noted that the swept source OCT is a method of imaging the morphology of an object by: scanning (sweeping) the wavelength of light that is irradiated to the object; acquiring the spectral intensity distribution by successively detecting interference light obtained from superposing the reflected lights of the light of the respective wavelengths on reference light; and executing Fourier transform on the acquired spectral intensity distribution. The en-face OCT is a method of irradiating light with a predetermined beam diameter to an object and analyzing the components of interference light obtained from superposing the reflected light thereof and reference light, thereby forming an image of a cross-section of the object orthogonal to the travelling direction of the light, and it is also referred to as full-field type.

An apparatus that is configured by combining an OCT apparatus and an retinal camera is explained in the following embodiment; however, the scope in which the present invention is applicable is not limited to such a combination apparatus. For example, the present invention may be applied to an apparatus with other combination or an ophthalmologic apparatus with a single function (for example, an OCT apparatus for imaging an eye fundus alone).

[Configuration]

Figure 1:
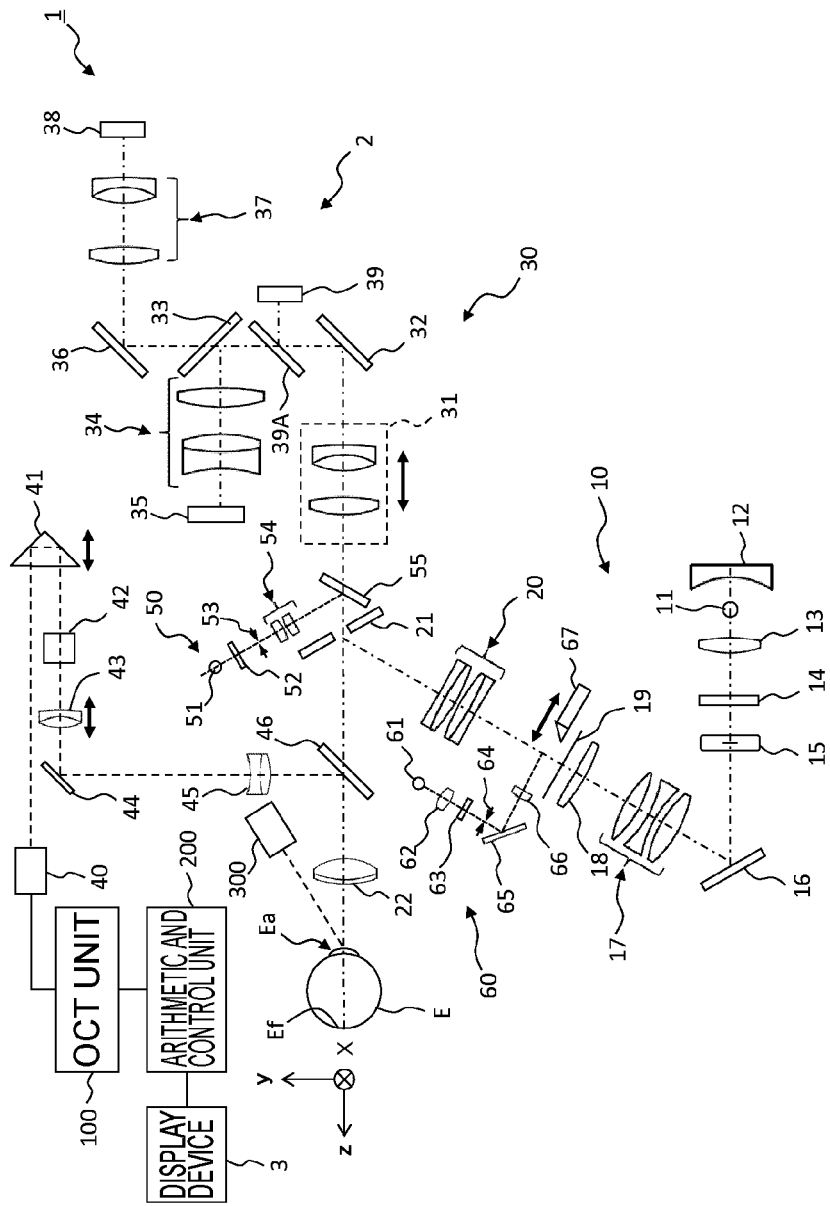
FIG. 1 is a schematic diagram showing an example of the configuration of an ophthalmologic apparatus according to an embodiment.

An ophthalmologic apparatus 1, as shown in FIG. 1, comprises a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a two-dimensional image (fundus image) representing the surface morphology of the fundus Ef of the eye E. Fundus images include observation images, captured images, etc. The observation image is, for example, a monochrome moving image formed at a prescribed frame rate using near-infrared light. It should be noted that when the optical system is focused on the anterior eye part Ea of the eye, the retinal camera unit 2 may obtain an observation image of the anterior eye part Ea. The captured image is, for example, a color image captured by flashing visible light, or a monochrome still image using near-infrared light or visible light as illumination light. The retinal camera unit 2 may be configured to be capable of acquiring other types of images such as a fluorescein angiography image, an indocyanine green fluorescent image and a fundus autofluorescent image.

A jaw holder and forehead rest for supporting the face of the subject is provided with the retinal camera unit 2. The jaw holder and forehead rest correspond to the supporter 440 indicated in FIG. 4A and FIG. 4B. It should be noted that, in FIG. 4A and FIG. 4B, symbol 410 indicates a base in which a drive system such as an optical system driver 2A, etc. and arithmetic and control circuits are accommodated. Moreover, symbol 420 indicates a case in which optical systems are accommodated, which is provided on the base 410. Moreover, symbol 430 indicates a lens case in which an objective lens 22 is accommodated, which is provided as a protrusion from the front surface of the case 420.

The retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors (sometimes simply called CCD) 35, 38). Moreover, the imaging optical system 30 guides signal light coming from the OCT unit 100 to the fundus Ef, and guides the signal light propagated through the fundus Ef to the OCT unit 100.

An observation light source 11 of the illumination optical system 10 comprises, for example, a halogen lamp. Light output from the observation light source 11 (observation illumination light) is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21, penetrates a dichroic mirror 46, and refracted by an object lens 22, thereby illuminating the fundus Ef. It should be noted that an LED (light emitting diode) may be used as the observation light source.

The fundus reflection light of the observation illumination light is refracted by the object lens 22, penetrates the dichroic mirror 46, passes through the aperture part formed in the center region of the aperture mirror 21, passes through a dichroic mirror 55, travels through a focusing lens 31, and is reflected by a mirror 32. Furthermore, the fundus reflection light passes through a half-mirror 39A, is reflected by a dichroic mirror 33, and forms an image on the light receiving surface of the CCD image sensor 35 by a condenser lens 34. The CCD image sensor 35 detects, for example, the fundus reflection light at a preset frame rate. An image (observation image) based on the fundus reflection light detected by the CCD image sensor 35 is displayed on a display device 3. It should be noted that when the imaging optical system 30 is focused on the anterior eye part, an observation image of the anterior eye part of the eye E is displayed.

The imaging light source 15 is configured, for example, by a xenon lamp. Light output from the imaging light source 15 (imaging illumination light) is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. An image (captured image) based on the fundus reflection light detected by the CCD image sensor 38 is displayed on the display device 3. It should be noted that the display device 3 for displaying an observation image and the display device 3 for displaying a captured image may be the same or different. Furthermore, when similar photographing is carried out by illuminating the eye E with infrared light, an infrared captured image is displayed. Moreover, an LED may be used as the imaging light source.

An LCD (Liquid Crystal Display) 39 displays a fixation target or a visual target for measuring visual acuity. The fixation target is a visual target for fixating the eye E, and is used when photographing a fundus or OCT measurement.

Part of the light output from the LCD 39 is reflected by a half-mirror 39A, reflected by the mirror 32, travels through the focusing lens 31 and the dichroic mirror 55, passes through the aperture part of the aperture mirror 21, penetrates the dichroic mirror 46, and is refracted by the object lens 22, thereby being projected to the fundus Ef.

By changing a display position of the fixation target on the screen of the LCD 39, a fixation position of the eye E is changed. Examples of the fixation position of the eye E includes a position for acquiring an image centered on the macula of the fundus Ef, a position for acquiring an image centered on the optic papilla, a position for acquiring an image centered on the fundus center between the macula and the optic papilla, etc. as in conventional retinal cameras, for example. Moreover, it is possible to arbitrarily change the display position of the fixation target.

Furthermore, as with conventional retinal cameras, the retinal camera unit 2 is provided with an alignment optical system 50 and a focus optical system 60. The alignment optical system 50 generates a target (alignment target) for position matching of the optical system (examination optical system) with respect to the eye E (alignment). The focus optical system 60 generates a target (split target) for adjusting the focus with respect to the eye E.

Light output from the LED 51 of the alignment optical system 50 (alignment light) travels through diaphragms 52, 53 and a relay lens 54, is reflected by the dichroic mirror 55, passes through the aperture part of the aperture mirror 21, penetrates the dichroic mirror 46, and is projected onto the cornea of the eye E by the object lens 22.

Cornea reflection light of the alignment light travels through the object lens 22, the dichroic mirror 46 and the abovementioned aperture part, and part of the cornea reflection light penetrates the dichroic mirror 55, passes through the focusing lens 31, is reflected by the mirror 32, penetrates the half-mirror 39A, is reflected by the dichroic mirror 33, and is projected onto the light receiving surface of the CCD image sensor 35 by the condenser lens 34. An image captured by the CCD image sensor 35 (alignment target) is displayed on the display device 3 along with the observation image. A user conducts alignment by an operation that is the same as conventional retinal cameras. Instead, alignment may be performed in such a way that an arithmetic and control unit 200 analyzes the position of the alignment target to move the optical system (automatic alignment). It should be noted that, in the present embodiment, automatic alignment is possible using anterior eye cameras 300 (mentioned later); therefore, the ability of automatic alignment using the alignment target is not necessarily required. However, it is possible to configure it such that automatic alignment may be carried out using the alignment target when automatic alignment using the anterior eye cameras 300 fails or the like, or to configure it such that automatic alignment using the anterior eye cameras 300 and automatic alignment using the alignment target may be selectively used.

In order to conduct focus adjustment, the reflection surface of a reflection rod 67 is arranged in a slanted position in the light path of the illumination optical system 10. Light output from an LED 61 of the focus optical system 60 (focus light) passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light travels through the relay lens 20, is reflected by the aperture mirror 21, penetrates the dichroic mirror 46, and is refracted by the object lens 22, thereby being projected on the fundus Ef.

The fundus reflection light of the focus light passes through the same route as the cornea reflection light of the alignment light and is detected by the CCD image sensor 35. An image captured by the CCD image sensor 35 (split target) is displayed on the display device 3 along with an observation image. The arithmetic and control unit 200, as in the conventional case, analyzes the position of the split target, and moves the focusing lens 31 and the focus optical system 60 for focusing (automatic focusing). It should be noted that focusing may be performed manually while visually recognizing the split target.

The dichroic mirror 46 branches the optical path for OCT measurement from the optical path for fundus photography. The dichroic mirror 46 reflects light of the wavelength band used in OCT measurement and transmits light for fundus photography. This optical path for OCT measurement is provided with, in order from the OCT unit 100 side, a collimator lens unit 40, an optical-path-length changing part 41, a galvano scanner 42, a focusing lens 43, a mirror 44, and a relay lens 45.

The optical-path-length changing part 41 is movable in the direction of the arrow indicated in FIG. 1, thereby changing the length of the optical path for OCT measurement. This change in the optical path length is used for correcting the optical path in accordance with the axial length of the eye E, adjusting the interference state, etc. The optical-path-length changing part 41 is configured to include, for example, a corner cube and a mechanism for moving this.

The galvano scanner 42 changes the travelling direction of light (signal light LS) travelling along the optical path for OCT measurement. Thereby, the fundus Ef may be scanned using the signal light LS. The galvano scanner 42 is configured to include, for example, a galvano mirror for scanning with the signal light LS in the x direction, a galvanometer mirror for scanning in the y direction, and a mechanism for independently driving these. Accordingly, the signal light LS may be scanned in any direction on the xy plane.

Figure 4A:
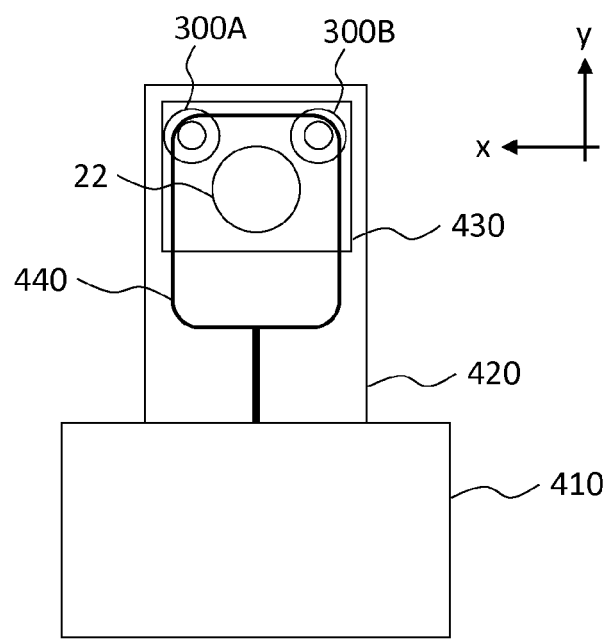
FIG. 4A is a schematic diagram showing an example of the configuration of an ophthalmologic apparatus according to an embodiment.
Figure 4B:
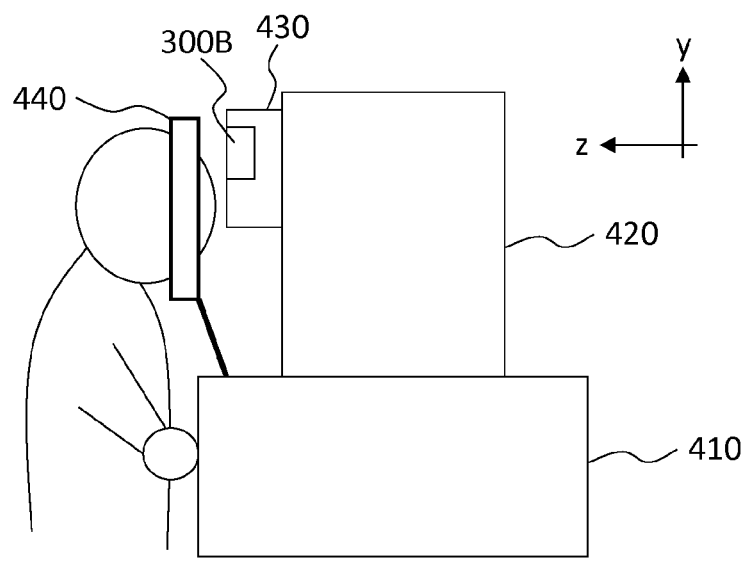
FIG. 4B is a schematic diagram showing an example of the configuration of an ophthalmologic apparatus according to an embodiment.

The retinal camera unit 2 is provided with anterior eye cameras 300. The anterior eye cameras 300 substantially simultaneously photograph an anterior eye part Ea from different directions. In the present embodiment, two cameras are provided on the surface of the retinal camera unit 2 of the subject side (refer to the anterior eye cameras 300A and 300B indicated in FIG. 4A). Moreover, the anterior eye cameras 300A and 300B are, as indicated in FIG. 1 and FIG. 4A, provided in positions away from the optical path of an illumination optical system 10 and the optical path of an imaging optical system 30. In other words, the anterior eye cameras 300A and 300B are non-coaxially arranged to the illumination optical system 10 and the imaging optical system 30. Hereinafter, the two anterior eye cameras 300A and 300B may be collectively represented by the symbol 300.

In the present embodiment, two anterior eye cameras 300A and 300B are provided; however, the number of anterior eye cameras in an embodiment may be any number of two or more (It should be noted that an anterior eye camera is not necessarily provided in the case of using an alignment target). However, when taking into consideration the arithmetic process (mentioned later), it is sufficient that a configuration is capable of substantially simultaneously photographing the anterior eye part from two different direction. Moreover, in the present embodiment, the anterior eye camera 300 is separately provided from the illumination optical system 10 and imaging optical system 30; however, the similar anterior-eye photography may be performed using at least the imaging optical system 30. That is, one from among two or more anterior eye cameras may be a configuration comprising the imaging optical system 30. In any case, it is sufficient in the present embodiment that the anterior eye part may be substantially simultaneously photographed from two (or more) different directions.

It should be noted that "substantially simultaneous" indicates allowing a time lag of the photographing timings by a degree of being able to ignore eye movements when photographing using two or more anterior eye cameras. Accordingly, images in which the eye E is in substantially the same position (direction) may be acquired by the two or more anterior eye cameras.

Moreover, photographing using the two or more anterior eye cameras may be a moving image photographing or a still image photographing; however, in the present embodiment, a case of carrying out moving image photographing is explained in greater detail. In the case of moving image photographing, substantial and simultaneous photographing of the anterior eye part mentioned above may be realized by means of controlling to match the timings for commencing photographing, or controlling frame rates and/or the timings for capturing respective frames. Further, it is possible to configure to associate signals substantially simultaneously input to the controller 210 (described later) from the two or more anterior eye cameras. Meanwhile, in the case of still image photographing, this may be realized by controlling so as to match the timings for photographing.

[OCT Unit]

Figure 2:
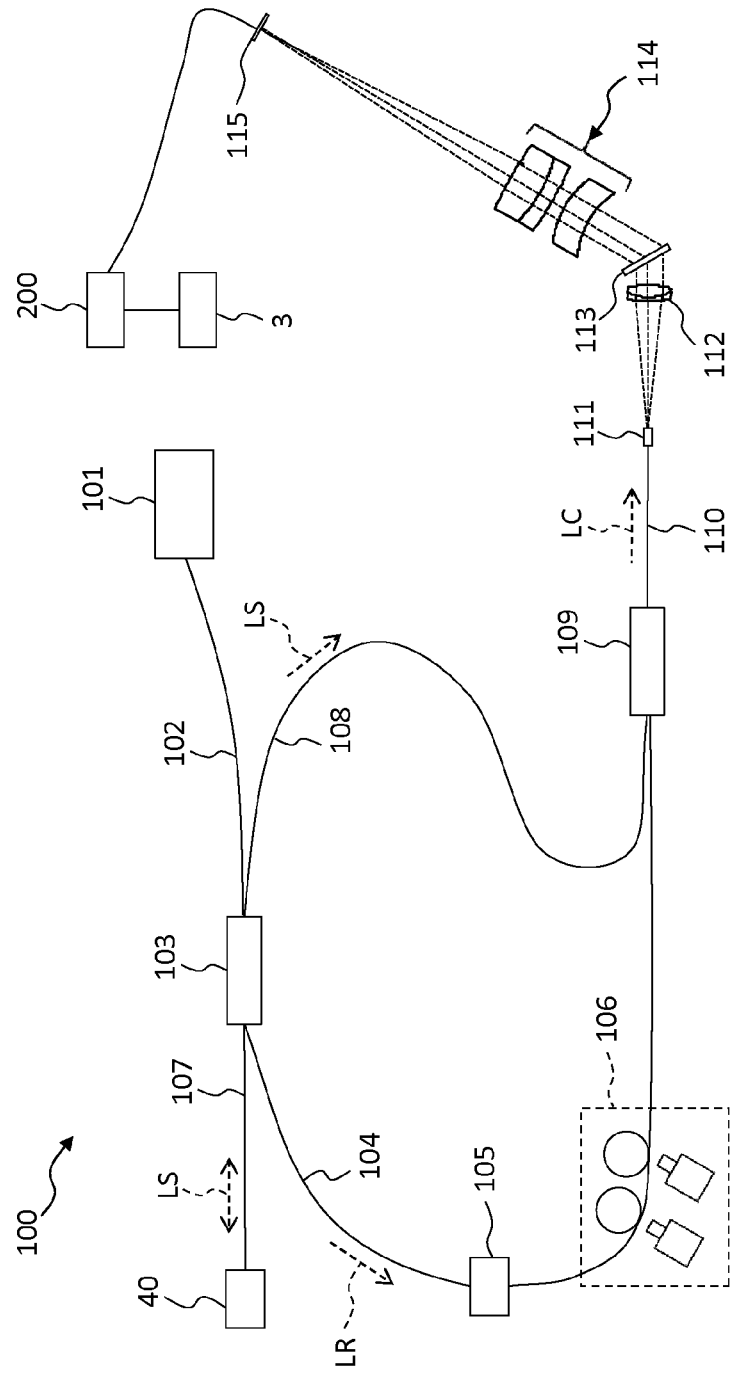
FIG. 2 is a schematic diagram showing an example of the configuration of an ophthalmologic apparatus according to an embodiment.

The configuration of the OCT unit 100 will be described with reference to FIG. 2. The OCT unit 100 is provided with an optical system for obtaining an OCT image of the fundus Ef. The optical system has a similar configuration to a conventional Fourier-domain-type OCT apparatus. That is to say, the optical system is configured to split light (e.g. low-coherence light) from a light source into reference light and signal light, make the signal light propagated through a fundus and the reference light propagated through a reference optical path interfere with each other to generate interference light, and detect the spectral component of this interference light. This detection result (detection signal) is transmitted to the arithmetic and control unit 200.

It should be noted that, in the case of swept source type OCT apparatus, a wavelength sweeping light source (swept source) is provided instead of a light source outputting low-coherence light, while an optical element for spectrally decomposing interference light is not provided. Generally, regarding the configuration of the OCT unit 100, known technologies may be applied according to the type of OCT.

The light source unit 101 outputs a broadband, low-coherence light L0. The low-coherence light L0 includes, for example, a near-infrared wavelength band (approximately 800 nm to 900 nm), and has a temporal coherence length of around several tens of micrometers. It should be noted that, a wavelength band that is not visible to human eyes, such as near-infrared light with a central wavelength of around 1040 to 1060 nm, for example, may be used as the low-coherence light L0.

The light source unit 101 is configured to include light output device, such as an SLD (super luminescent diode), LED, SOA (Semiconductor Optical Amplifier) and the like.

The low coherence light L0 output from the light source unit 101 is guided to a fiber coupler 103 by an optical fiber 102 and split into signal light LS and reference light LR.

The reference light LR is guided by the light fiber 104 and arrives at an optical attenuator (attenuator) 105. The optical attenuator 105 automatically adjusts the light amount of the reference light LR guided by the light fiber 104 under the control of the arithmetic and control unit 200 using known technologies. The reference light LR with the light amount having adjusted by the optical attenuator 105 is guided by the light fiber 104, arriving at a polarization adjuster (polarization controller) 106. The polarization adjuster 106 is an apparatus that, by means of applying external stress to a looped light fiber 104, adjusts the polarization condition of the reference light LR guided in the light fiber 104. It should be noted that the configuration of the polarization adjuster 106 is not limited to this and any known technologies may be used. The reference light LR with adjusted polarization condition by the polarization adjuster 106 arrives at the fiber coupler 109.

The signal light LS generated by the fiber coupler 103 is guided by the light fiber 107 and becomes a parallel light flux by means of the collimator lens unit 40. Further, the signal light LS arrives at the dichroic mirror 46 via the optical-path-length changing part 41, the galvano scanner 42, the focusing lens 43, the mirror 44, and the relay lens 45. Subsequently, the signal light LS is reflected by the dichroic mirror 46, refracted by the objective lens 22, and projected onto the fundus Ef. The signal light LS is scattered (including reflections) at various depth positions of the fundus Ef. A back-scattered light of the signal light LS from the fundus Ef reversely advances along the same path as the outward path and is guided to the fiber coupler 103, arriving at the fiber coupler 109 via the light fiber 108.

The fiber coupler 109 causes the back-scattered light of the signal light LS and the reference light LR having passed through the optical fiber 104 to interfere with each other. Interference light LC thus generated is guided by an optical fiber 110 and output from an exit end 111. Furthermore, the interference light LC is converted to a parallel light flux by a collimator lens 112, spectrally divided (spectrally decomposed) by a diffraction grating 113, converged by the convergence lens 114, and projected onto the light receiving surface of a CCD image sensor 115. It should be noted that although the diffraction grating 113 shown in FIG. 2 is of the transmission type, it is possible to use a spectrally decomposing element of any other type, such as a diffraction grating of reflection type.

The CCD image sensor 115 is for example a line sensor, and detects the respective spectral components of the spectrally decomposed interference light LC and converts the components into electric charges. The CCD image sensor 115 accumulates these electric charges to generate a detection signal, and transmits the signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. An arithmetic process for this is the same as that of a conventional Fourier-domain-type OCT apparatus.

Further, the arithmetic and control unit 200 controls each part of the retinal camera unit 2, the display device 3 and the OCT unit 100. For example, the arithmetic and control unit 200 causes the display device 3 to display an OCT image G of the fundus Ef.

Moreover, as control of the retinal camera unit 2, the arithmetic and control unit 200 executes: control of actions of the observation light source 11, the imaging light source 15 and the LED's 51 and 61; control of action of the LCD 39; control of movements of the focusing lenses 31 and 43; control of movement of the reflection rod 67; control of movement of the focus optical system 60; control of movement of the optical path length changing part 41; control of action of the galvano scanner 42; control of actions of the anterior eye cameras 300; and so on.

Further, as control of the OCT unit 100, the arithmetic and control unit 200 executes: control of action of the light source unit 101; control of action of the optical attenuator 105; control of action of the polarization adjuster 106; control of action of the CCD image sensor 115; and so on.

The arithmetic and control unit 200 includes a microprocessor, a RAM, a ROM, a hard disk drive, a communication interface, and so on, as in conventional computers. The storage device such as a hard disk drive stores computer programs for controlling the ophthalmologic apparatus 1. The arithmetic and control unit 200 may be provided with various kinds of circuit boards, such as a circuit board for forming OCT images. Moreover, the arithmetic and control unit 200 may be provided with operation devices (input devices) such as a keyboard and a mouse, and/or display devices such as an LCD.

The retinal camera unit 2, the display device 3, the OCT unit 100, and the arithmetic and control unit 200 may be integrally configured (that is, within a single case), or configured as two of more separated cases.

[Control System]

Figure 3:
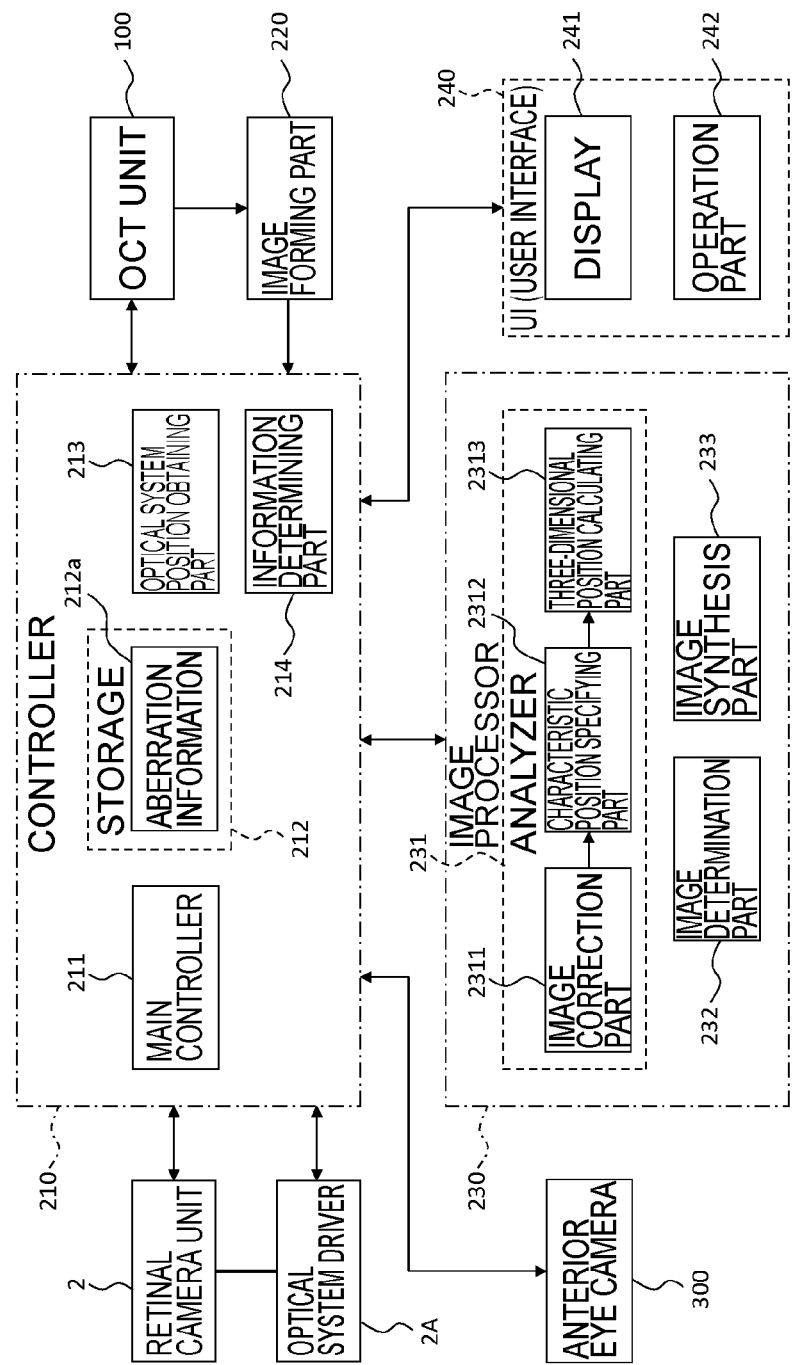
FIG. 3 is a schematic diagram showing an example of the configuration of an ophthalmologic apparatus according to an embodiment.

A configuration of a control system of the ophthalmologic apparatus 1 will be described with reference to FIG. 3.

(Controller)

The control system of the ophthalmologic apparatus 1 has a configuration with a controller 210 as a center. The controller 210 includes, for example, the aforementioned microprocessor, RAM, ROM, hard disk drive, and communication interface. The controller 210 is provided with a main controller 211, a storage 212, an optical system position obtaining part 213 and an information determining part 214.

(Main Controller)

The main controller 211 carries out various kinds of controls mentioned above. It should be noted that the movement control of the focusing lens 31 is configured to control a focus driver (not illustrated) to move the focusing lens 31 in the optical axis direction. Thereby, the focus position of the imaging optical system 30 is changed. Moreover, control of the motion of the focusing lens 43 is to move the focusing lens 43 in the optical axis direction by controlling a focus driver (not illustrated). Thereby, focus position of the signal light LS is changed.

The main controller 211 is capable of controlling the optical system driver 2A to three-dimensionally move the optical system installed in the retinal camera unit 2. This control is carried out upon automatic alignment and/or tracking. Here, tracking refers to moving the optical system of the apparatus in accordance with the eye movement of the eye E. Tracking is carried out at, for example, the stage after alignment (depending on the conditions, focusing is also carried out in advance). Tracking is a function causing the position of the optical system of the apparatus to follow the eye movement, thereby maintaining a suitable positional relationship in which alignment (and focusing) is matched.

It should be noted that the optical system driver 2A of the present embodiment moves the optical system installed in the retinal camera unit 2; however, a configuration is possible in which the optical system installed in the retinal camera unit 2 and the optical system installed in the OCT unit 100 are moved by means of the optical system driver 2A.

Moreover, the anterior eye cameras 300 of the present embodiment are provided on the case of the retinal camera unit 2; accordingly, the anterior eye cameras 300 can be moved by means of controlling the optical system driver 2A (camera moving part). Moreover, it is possible to provide a camera moving part capable of independently moving the two or more anterior eye cameras 300, respectively. Specifically, the camera moving part may be configured to include driving mechanisms (actuator, power transmission mechanism, etc.) provided with respect to each anterior eye camera 300. Moreover, the camera moving part may be configured to move two or more anterior eye cameras 300 by transmitting the power generated by a single actuator by means of the power transmission mechanism provided for each anterior eye camera 300.

The main controller 211 executes a process of writing data into the storage 212, and a process of reading out data from the storage 212.

The storage 212 stores various kinds of data. The data stored in the storage 212 is, for example, image data of OCT images, image data of fundus images, and eye information. The eye information includes information on a subject such as a patient ID and a name, information on an eye such as identification information of left eye or right eye, and so on. Moreover, various kinds of programs and data in order to operate the ophthalmologic apparatus 1 are stored in the storage 212.

Aberration information 212a is stored in the storage 212 in advance. The aberration information 212a includes information, for each anterior eye camera 300, regarding the distortion aberration occurred in a photograph image due to effects by the optical system installed therein. Here, the optical system installed in the anterior eye camera 300 includes, for example, optical elements occurring distortion aberration of lenses, etc. It may be said that the aberration information 212a is a parameter that quantifies the deformation of the photograph images caused by these optical elements.

An example of a method for generating the aberration information 212a is explained. Taking into consideration instrumental error (difference in distortion aberration) of the anterior eye cameras 300, the following measurements are carried out for each anterior eye camera 300. An operator prepares specific reference points. The reference points are photographing target used in detecting the distortion aberration. The operator performs photographing multiple times while changing the relative position between the reference points and the anterior eye cameras 300. Accordingly, multiple photograph images of the reference points photographed from different directions may be obtained. The operator analyzes the multiple acquired photograph images, thereby generating the aberration information 212a of this anterior eye camera 300. It should be noted that the computer that performs this analysis process may be an image processor 230 or any other computer (computer for inspection before shipping products, computer for maintenance, etc.).

The analysis processes for generating the aberration information 212a include, for example, the following procedures:

an extraction procedure for extracting image regions corresponding to the reference points in each photograph image;

a distribution state calculating procedure for calculating the distribution state (coordinates) of the image regions corresponding to the reference points in each photograph image;

a distortion aberration calculating procedure for calculating a parameter indicating the distortion aberration based on the obtained distribution state; and a correction factor calculating procedure for calculating a factor for correcting the distortion aberration based on the obtained parameter.

It should be noted that the parameter related to the distortion aberration that is given to an image by the optical system may include the principal distance, the position of a principal point (vertically and horizontally), the distortion of a lens (radiation direction and tangential direction), etc. The aberration information 212a is constructed as information (for example, table information) that associates the identification information of each anterior eye camera 300 and the correction factor corresponding thereto. The aberration information 212a generated in this manner is stored in the storage 212 by the main controller 211. Generation of such aberration information 212a and the aberration correction process based on this is referred to as camera calibration, etc.

(Optical System Position Obtaining Part)

The optical system position obtaining part 213 obtains the current position of the examination optical system installed in the ophthalmologic apparatus 1. The examination optical system is the optical system used for optically examining the eye E. The examination optical system in the ophthalmologic apparatus 1 of the present embodiment (combined machine of the retinal camera and OCT apparatus) is the optical system for obtaining images of an eye.

The optical system position obtaining part 213 receives information presenting the content of the movement control of the optical system driver 2A by means of the main controller 211, and obtains the current position of the examination optical system moved by the optical system driver 2A. A detailed example of this process will be explained. The main controller 211 controls the optical system driver 2A at a predetermined timing (upon start-up of the apparatus, upon inputting patient information, etc.) and moves the examination optical system to a predetermined initial position. Thereafter, the main controller 211 stores the control content each time the optical system driver 2A is controlled. Thereby, a history of the control contents may be obtained. The optical system position obtaining part 213 refers to this history and obtains the control contents to date, and determines the current position of the examination optical system based on these control contents.

Moreover, each time the main controller 211 controls the optical system driver 2A, the control contents thereof may be transmitted to the optical system position obtaining part 213, and the current position of the examination optical system may be obtained each time the optical system position obtaining part 213 receives the control contents.

As another configuration example, the position sensor detecting the position of the examination optical system may be provided with the optical system position obtaining part 213.

When the current position of the examination optical system is obtained by the optical system position obtaining part 213 as stated above, the main controller 211 is capable of, based on the obtained current position and the three-dimensional position of the eye E obtained by an analyzer 231 (mentioned later), causing the optical system driver 2A to move the examination optical system. Specifically, the main controller 211 recognizes the current position of the examination optical system from the acquisition result by the optical system position obtaining part 213, and recognizes the three-dimensional position of the eye E from the analysis result by the analyzer 231. Subsequently, in order that the position of the examination optical system with respect to the three-dimensional position of the eye E becomes a predetermined positional relationship, the main controller 211 changes the position thereof with the current position of the examination optical system as the starting point. This predetermined positional relationship may be such that the positions in the x and y directions respectively coincide, while the distance in the z direction becomes a predetermined working distance. The working distance is a preset value, and it means the distance between the eye E and the examination optical system when performing examination using the examination optical system.

(Information Determining Part)

The information determining part 214 determines whether or not information obtained from OCT is appropriate for carrying out OCT. the information obtained from OCT may be a detection signal from the CCD image sensor 115 of the OCT unit 100, or information obtained by executing a prescribed process on this detection signal. Examples of the latter include the following information: a cross sectional image (e.g. A-scan image, two-dimensional cross sectional image) formed by an image forming part 220 based on the detection signals; information obtained in the halfway stage of this cross sectional image formation; information (e.g. image etc.) formed by the image processor 230 based on one or more cross sectional images; information obtained by executing a process other than these on the detection signal.

An example of a determination process based on a detection signal from the CCD image sensor 115 is explained. The information determining part 214 analyzes the detection signal to derive information indicating a characteristic thereof (characteristic information), and determines whether or not this characteristic information is appropriate for carrying out OCT. Types of the characteristic information may be determined in advance based on an influence on the signal light LS (that is, an influence on the interference light LC) from an intraocular factor that disturbs light.

Intensity (amplitude etc.) is an example of the characteristic information. For example, when the signal light LS passes through an opaque portion in the eye E, the intensity of the signal light LS decreases, thereby the intensity of the interference light LC decreases. The information determining part 214 derives the intensity of the detection signal obtained by detecting the interference light LC, and compares this intensity with a threshold. When the intensity is equal to or less than the threshold, the information determining part 214 determines that this detection signal is not appropriate. This threshold is defined in advance, for example, based on the intensity of light output from the light source unit 101. It should be noted that the threshold may be defined by taking account of various factors such as the light splitting ratio of the fiber coupler 103, light attenuation amounts by optical elements, or the standard attenuation amount of light that passes through a healthy eye. Moreover, an amount of noises and SN ratio are examples of the characteristic information other than signal intensity.

Even when taking account of information obtained in the halfway stage of the cross sectional image formation or information obtained by executing a process other than image formation on the detection signal, it is capable of applying a similar process to the case of taking account of the detection signal. Moreover, the same applies to the case of taking account of information generated by the image processor 230 (for example, information other than images) based on one or more cross sectional images formed by the image forming part 220.

Examples of determination processes in the case of taking account of a cross sectional image (A-scan image, two-dimensional cross sectional image, etc.) formed by the image forming part 220 or a cross sectional image (three-dimensional image etc.) formed by the image processor 230. A two-dimensional or three-dimensional cross sectional image is obtained by changing the irradiation position of the signal light LS on the fundus Ef (that is, by scanning the fundus Ef with the signal light LS). If there is an opaque portion on at least a part of the trajectory of the scanning, there are cases in which the image quality of the A-scan image (one-dimensional image along the depth direction) based on the signal light LS having passed the opaque portion is deteriorated, or even the fundus Ef is not imaged.

The information determining part 214 analyzes respective A-scan images included in a cross sectional image to calculate an evaluation value of image quality, and compares this evaluation value with a threshold. When the evaluation value is equal to or less than the threshold, the information determining part 214 determines that this A-scan image is not appropriate. The information determining part 214 carries out this process for all A-scan images, thereby obtaining the distribution of A-scan images (that is, scanning positions) determined to be appropriate and A-scan images (that is, scanning positions) determined to be not appropriate.

It should be noted that this threshold may be defined in advance, or set in the determination process. As an example of the latter, the threshold may be defined by statistically processing distribution (e.g. histogram) of multiple evaluation values calculated in the determination process.

Moreover, the evaluation value may be an arbitrary index indicating image quality of an A-scan image. For example, it is possible to obtain the evaluation value based on distribution of brightness in an A-scan image. As a specific example thereof, it is possible to derive, as an evaluation value, the contrast of an A-scan image, such as the difference or ratio between high brightness parts (pixels corresponding to tissues with high reflectance) and low brightness parts (pixels corresponding to tissues with low reflectance).

Another example of a process carried out by the information determining part 214 is explained. This determination process determines whether the process called Auto-Z has succeeded or failed. The Auto-Z is a function for depicting the image of the fundus Ef within a prescribed area (target area) in the frame of an OCT image (cross sectional image).

In the Auto-Z, the same positions of the fundus Ef are repeatedly scanned. The trajectory of the respective scans is, for example, of linear shape (line scanning). The information determining part 214 analyzes each of the cross sectional images that are successively acquired by the repetitive scanning, thereby specifying, in real time, the depthwise position (position in the z-direction (depthwise direction)) in the frame at which the image of a prescribed tissue (e.g. the surface of the fundus, a layer tissue with high brightness) of the fundus Ef is depicted. Furthermore, the information determining part 214 calculates the displacement between the specified depthwise position and the target area. The main controller 211 adjusts the difference of the optical path length between the signal light LS and the reference light LR such that the calculated displacement is cancelled, that is, such that the image of the prescribed tissue is depicted in the target area.

The adjustment of the difference of the optical path length is carried out by controlling the optical-path-length changing part 41 to change the optical path length of the signal light LS. It should be noted that it is possible to apply a configuration to change the optical path length of the reference light LR (for example, a variable reference mirror (described later)). Moreover, it is possible to apply both the a configuration for changing the optical path length of signal light and a configuration for changing the optical path length of reference light.

The main controller 211 and the information determining part 214 carry out the above-mentioned process for the respective cross sectional images (or thinning-out of the cross sectional images is applied) obtained by the repetitive scanning. When the above-mentioned displacement becomes equal to or less than the threshold by a prescribed timing, that is, when the image of the prescribed tissue is depicted within the target area by the prescribed timing, the information determining part 214 determines that the Auto-Z succeeds.

In contrast, when the above-mentioned displacement does not become equal to or less than the threshold by the prescribed timing, that is, when the image of the prescribed tissue is not depicted within the target area by the prescribed timing, the information determining part 214 determines that the Auto-Z is failed. It should be noted that this prescribed timing is set in advance, and may be defined as the number of times of comparison between the above-mentioned displacement and the threshold, or as the elapsed time from the beginning of the Auto-Z.

In the present example, the success (or failure) of the Auto-Z corresponds to the fact that information obtained by the optical system is appropriate (or not appropriate) for performing OCT. It should be noted that scattering or absorption of the signal light LS due to an opaque portion of the eye E is considered as a factor of failure of the Auto-Z.

The information determining part 214 may be configured to carry out a determination process based on any evaluation value relating the image quality of a cross sectional image instead of the success/failure of the Auto-Z.

(Image Forming Part)

The image forming part 220 forms image data of a cross sectional image of the fundus Ef based on the detection signals from the CCD image sensor 115. Like the conventional spectral-domain-type OCT, this process includes processes such as noise elimination (noise reduction), filtering and FFT (Fast Fourier Transform). In the case of other types of OCT apparatus, the image forming part 220 executes known processes in accordance with the type thereof.

The image forming part 220 is configured to include, for example, the aforementioned circuit boards. It should be noted that "image data" and the "image" based on this may be identified with each other in this specification.

(Image Processor)

The image processor 230 executes various image processes and analysis on images formed by the image forming part 220. For example, the image processor 230 executes various correction processes such as luminance correction and dispersion compensation of images. Moreover, the image processor 230 executes various image processes and analysis on images (fundus images, anterior eye images, etc.) obtained by the retinal camera unit 2.

The image processor 230 executes known image processes such as an interpolation process of interpolating pixels between cross sectional images, thereby forming a three-dimensional image data of the fundus Ef. The three-dimensional image data refers to image data that the positions of pixels are defined by the three-dimensional coordinates. The three-dimensional image data is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data to form image data of a pseudo three-dimensional image taken from a specific view direction. This pseudo three-dimensional image is displayed on the display 241.

Further, it is also possible to form stack data of multiple cross sectional images as a three-dimensional image data. Stack data is image data obtained by three-dimensionally arranging multiple cross sectional images obtained along multiple scanning lines, based on the positional relation of the scanning lines. That is to say, stack data is image data obtained by expressing multiple cross sectional images defined by originally individual two-dimensional coordinate systems by a three-dimensional coordinate system (namely, embedding into a three-dimensional space).

Further, the image processor 230 may form a cross sectional image at an arbitrary cross section based on a three-dimensional image data. This process is called MPR (Multi-Planar Reconstruction) and the like, and includes a process of extracting picture elements (voxels) located at a designated cross section and a process of arranging the extracted picture elements.

Further, the image processor 230 is provided with an analyzer 231, an image determination part 232, and an image synthesis part 233.

(Analyzer)

The analyzer 231 analyzes two or more photograph images substantially simultaneously obtained by two or more anterior eye cameras 300, thereby obtaining the three-dimensional position of the eye E. As an example of a configuration for performing this process, the analyzer 231 is provided with an image correction part 2311, characteristic position specifying part 2312, and a three-dimensional position calculating part 2313.

(Image Correction Part)

The image correction part 2311 corrects the distortion of each photograph image obtained by the anterior eye cameras 300 based on the aberration information 212a stored in the storage 212. This process may be carried out by, for example, known image process technology based on a correction factor for correcting distortion aberration. It should be noted that, for cases in which the distortion aberration caused in photograph images due to the optical system of the anterior eye cameras 300 is sufficiently small, etc., there is no need to provide the aberration information 212a and the image correction part 2311.

(Characteristic Position Specifying Part)

The characteristic position specifying part 2312 analyzes each photograph image (with the distortion aberration corrected by the image correction part 2311), thereby specifying the position in the photograph image corresponding to the predetermined characteristic part of the anterior eye part Ea (referred to as the characteristic position). As the predetermined characteristic part, for example, the center of the pupil or the corneal apex of the eye E may be used. Hereinafter, a specific example of a process for specifying the center of the pupil is explained.

First, the characteristic position specifying part 2312 specifies the image region (pupillary region) corresponding to the pupil of the eye E based on the distribution of the pixel values (luminous values, etc.) in a photograph image. Generally, the pupil is represented with lower luminance compared to other parts, so the pupillary region may be specified by searching an image region with low luminance. At this time, the pupillary region may be specified taking into consideration the shape of the pupil. That is, a configuration is possible of specifying the pupillary region by means of searching a substantially circular image region with low luminance.

Next, the characteristic position specifying part 2312 specifies the center position of the specified pupillary region. As mentioned above, the pupil is substantially circular; therefore, it is possible to specify the contour of the pupillary region, specify the center position of this contour (an approximate circle or an approximate ellipse thereof), and treat this as the center of the pupil. Instead, it is possible to derive the center of gravity of the pupillary region and treat this center of gravity as the center of the pupil.

It should be noted that even when specifying the characteristic position corresponding to other characteristic part, it is possible to specify the characteristic position based on the pixel value distribution of the photograph image in the same manner as those mentioned above.

(Three-Dimensional Position Calculating Part)

The three-dimensional position calculating part 2313 calculates the three-dimensional position of the eye E based on the positions of two or more anterior eye cameras 300 and the characteristic positions in the two or more photograph images specified by the characteristic position specifying part 2312. This process is explained with reference to FIG. 5A and FIG. 5B.

Figure 5A:
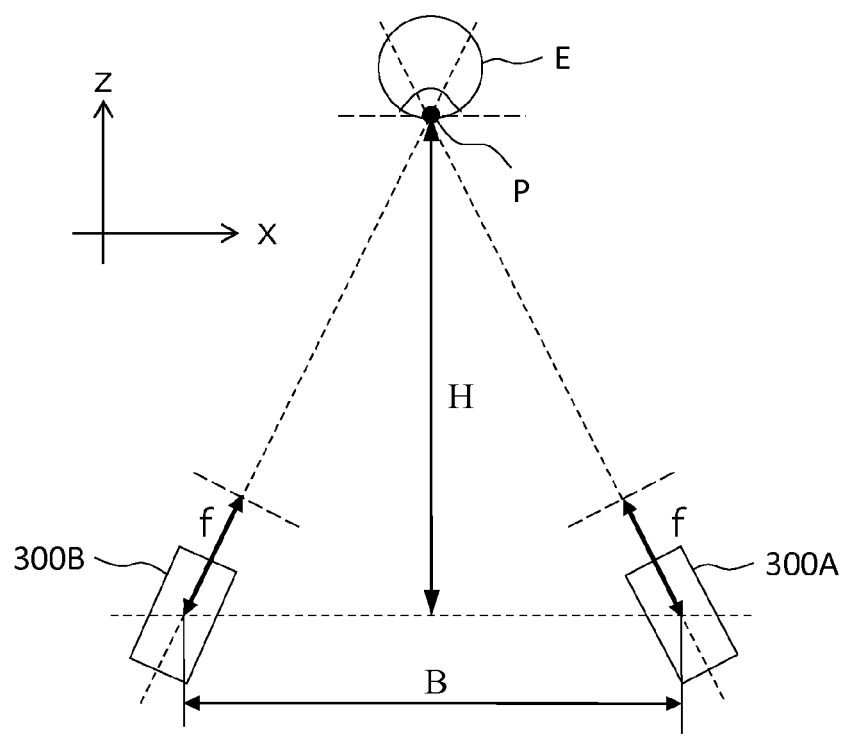
FIG. 5A is a schematic diagram for explaining an operational example of an ophthalmologic apparatus according to an embodiment.
Figure 5B:
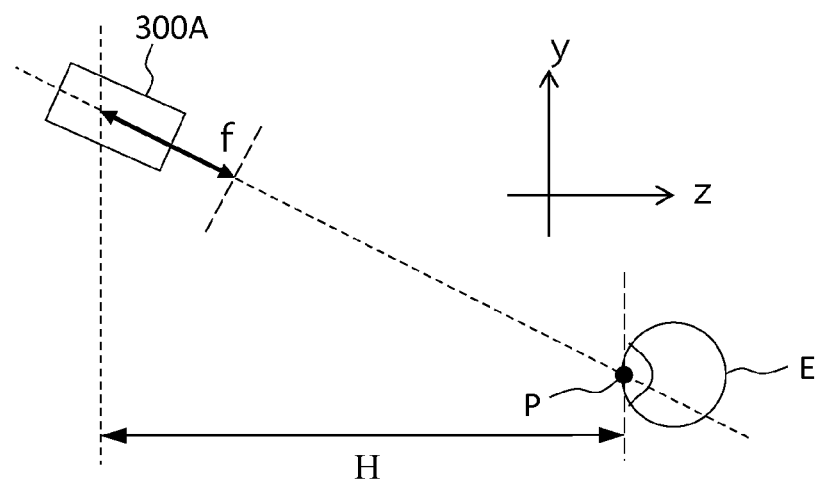
FIG. 5B is a schematic diagram for explaining an operational example of an ophthalmologic apparatus according to an embodiment.

FIG. 5A is a top view illustrating the positional relationship between the eye E and the anterior eye cameras 300A and 300B. FIG. 5B is a side view illustrating the positional relationship between the eye E and the anterior eye cameras 300A and 300B. The distance (base line length) between the two anterior eye cameras 300A and 300B is represented as "B." The distance (photographing distance) between the base line of the two anterior eye cameras 300A and 300B and a characteristic part P of the eye E is represented as "H." The distance (screen distance) between the respective anterior eye cameras 300A and 300B and a screen plane thereof is represented as "f."

In such an arrangement state, the resolution of images photographed by the anterior eye cameras 300A and 300B is expressed by the following formula. Here, $\Delta p$ represents the pixel resolution.

$xy$ resolution (planar resolution): $\Delta xy = H \times \Delta p / f$ $z$ resolution (depth resolution): $\Delta z = H \times H \times \Delta p / (B \times f)$ The three-dimensional position calculating part 2313 applies known trigonometry, taking into consideration the positional relationship indicated in FIG. 5A and FIG. 5B, to the positions of the two anterior eye cameras 300A and 300B (these are known) and the characteristic positions corresponding to the characteristic part P in the two photograph images, thereby calculating the three-dimensional position of the characteristic part P, that is, the three-dimensional position of the eye E.

The three-dimensional position of the eye E calculated by the three-dimensional position calculating part 2313 is transmitted to the controller 210. Based on this calculation result of the three-dimensional position, the controller 210 controls the optical system driver 2A such that the optical axis of the examination optical system matches the axis of the eye E and such that the distance of the examination optical system with respect to the eye E becomes the predetermined working distance.

Moreover, when the anterior eye cameras 300 parallelly photograph moving images of the anterior eye part Ea from different directions, tracking of the examination optical system with respect to the movement of the eye E becomes possible by carrying out, for example, the following processes (1) and (2).

(1) The analyzer 231 successively analyzes the two or more frames substantially simultaneously obtained by photographing moving pictures using two or more anterior eye cameras 300, thereby successively obtaining the three-dimensional positions of the eye E.

(2) The controller 210 successively controls the optical system driver 2A based on the three-dimensional positions of the eye E successively obtained by the analyzer 231, thereby causing the position of the examination optical system to follow the movement of the eye E.

The analyzer 231 may derive the displacement between the eye E and the examination optical system based on the three-dimensional position obtained by the three-dimensional position calculating part 2313. This process may be carried out by utilizing the fact that the positions of the anterior eye cameras 300 and the position of the examination optical system are known. Here, the position of the examination optical system is a position given in advance, and is, for example, the intersecting position of the front surface (surface facing the eye E) of the objective lens 22 and the optical axis of the examination optical system.

Another example of a process for deriving the displacement between the eye E and the examination optical system is explained. In the present example, the alignment target is projected on the anterior eye part of the eye E. Further, a moving picture of the anterior part on which the alignment target is being projected is acquired by the retinal camera unit 2. In general, a pair of alignment targets is displayed in each of the frames of this moving picture. The analyzer 231 calculates the objective displacement based on the displayed position of the pair of the alignment targets.

This process is explained more specifically. When the examination optical system is positioned in a prescribed examination position relative to the eye E, the pair of the alignment targets is displayed over a prescribed position of the frame (for example, the center of the frame). The examination position corresponds to the positional relationship between the eye E and the examination optical system such that, for example, the x-coordinate and the y-coordinate of the prescribed site of the eye E (e.g. the corneal apex, the center of the pupil) and the x-coordinate and the y-coordinate of the examination optical system are substantially equal, and such that the distance between the eye E and the examination optical system (e.g. the objective lens 22) is substantially equal to the prescribed working distance. Further, the gap (first gap) between the displayed positions of the two alignment targets reflects the displacement from the working distance in the z-direction, and the gap (second gap) of the displayed positions of the alignment targets relative to the prescribed position of the frame reflects the displacement from the prescribed site of the eye E in the xy-direction. The analyzer 231 utilizes this relationship to derive the displacement in the z-direction from the first gap and the displacement in the xy-direction from the second gap. Thereby, the three-dimensional displacement between the eye E and the examination optical system is obtained. It should be noted that such a process for calculating a displacement is a process carried out in a known automatic alignment.

(Image Determination Part)

The image determination part 232 analyzes a photograph image(s) obtained by at least one from among two or more anterior eye cameras 300, thereby determining whether or not the image of the anterior eye part Ea is within the predetermined area in this photograph image(s).

This predetermined area is set in advance within the photographing region of the anterior eye camera 300, for example, set as a region including the center of this photographing region. Here, the range of this predetermined area may be changed in accordance with the photographing conditions of the anterior eye camera 300 (the position, the photographic magnification, etc. of the anterior eye camera 300). Moreover, the range of this predetermined area may be determined in accordance with the setting of a characteristic point (mentioned later). Moreover, the predetermined area may be set so as to correspond to the position of the supporter 440 (jaw holder, forehead rest, etc.; refer to FIG. 4A and FIG. 4B.) supporting the face of the subject or the vicinity position thereof.

A detailed example of the process carried out by the image determination part 232 is explained. First, the image determination part 232 specifies the image region corresponding to the predetermined characteristic point of the anterior eye part Ea from the photograph image. This characteristic point may be the center of the pupil, the contour of the pupil, the center of the iris, the contour of the iris, the corneal apex, etc. The process of specifying the image region corresponding to the characteristic point is carried out similarly to, for example, the process carried out by the characteristic position specifying part 2312. It should be noted that when the characteristic point and the characteristic part are the same, the specification result by the characteristic position specifying part 2312 may be used in the process carried out by the image determination part 232.

Next, the image determination part 232 judges whether or not the specified characteristic point is within the predetermined area of the photograph image (the frame thereof). This process may be carried out by comparing the coordinates corresponding to the predetermined area and the coordinates of the characteristic point.

The image determination part 232 transmits this determination result to the controller 210. When it is determined that the image of the anterior eye part Ea is not included in the predetermined area, the controller 210 controls the optical system driver 2A (camera moving part) to move the anterior eye cameras 300 in a direction away from the supporter 440 (that is, the face of the subject) and/or a direction outwards of the supporter 440. The direction away from the supporter 440 is the −z direction in the coordinate system indicated in FIG. 1, etc. Moreover, the direction outwards of the supporter 440 is the direction in which the anterior eye cameras 300 moves away from the optical axis of the examination optical system. The direction away from the examination optical system may be defined horizontally (±x direction) and/or vertically (±y direction). That is, the direction away from the examination optical system may be defined in any direction in the xy plane.

Moreover, the moving direction and/or the moving distance of the anterior eye camera 300 may be set based on, for example, the positional relationship between the anterior eye camera 300 and the supporter 440 before movement. Moreover, a configuration is possible of alternately carrying out the determination process by the image determination part 232 and the moving process of the anterior eye camera 300, thereby controlling so as to improve the position of the anterior eye camera 300 toward a suitable position. Moreover, a configuration is possible of determining the moving direction and/or the moving distance of the anterior eye camera 300 in accordance with the distance (number of pixels) between the image region corresponding to the characteristic point and the predetermined area. Moreover, a configuration is possible of determining the moving direction and/or the moving distance of the anterior eye camera 300 in accordance with the distance between the image region corresponding to the characteristic point and the predetermined position (for example, the center position) in the predetermined area.

Other operation examples based on the determination result by the image determination part 232 are explained. When it is determined that the image of the anterior eye part Ea is not included in the predetermined area, the controller 210 causes an output part to output a predetermined warning information. This output part may be the display 241, an audio output part (not illustrated), etc. When using the display 241 as the output part, the controller 210 causes the display 241 to display a warning message including a predetermined text string information, image information, pop-up window, etc. When the audio output part is used as the output part, the controller 210 causes the audio output part to output the predetermined voice information, warning sound, etc.

From such warning information, the user recognizes that the image of the anterior eye part Ea is not included in the predetermined area. Subsequently, the user can use the operation part 242 to three-dimensionally move the anterior eye camera 300. Further, the controller 210 may output information (movement information) indicating the moving direction and/or the moving distance of the anterior eye camera 300 together with a warning information. This movement information is generated based on, for example, the positional relationship between the image region corresponding to the characteristic point obtained by the image determination part 232 and the predetermined area. A configuration is possible wherein the determination process is carried out again by the image determination part 232 once the manual movement by the user is completed.

(Image Synthesis Part)

The image synthesis part 233 forms a synthetic image of the two or more photograph images that are substantially simultaneously obtained by two or more anterior eye cameras 300. A stereoscopic image and an image obtained from viewpoint conversion (viewpoint-converted image) based on the two or more photograph images are examples of the synthetic image. The viewpoint of the viewpoint-converted image is set on, for example, the optical axis of the examination optical system. These synthetic images may be obtained by using any known image synthesizing process.

The image processor 230 that functions as above includes, for example, the aforementioned microprocessor, RAM, ROM, hard disk drive, circuit board, and so on. Computer programs that cause a microprocessor to execute the above functions are previously stored in a storage device such as a hard disk drive.

(User Interface)

A user interface 240 includes the display 241 and the operation part 242. The display 241 is configured including the aforementioned display device of the arithmetic and control unit 200 and the display device 3. The operation part 242 is configured including the aforementioned operation device of the arithmetic and control unit 200. The operation part 242 may include various kinds of buttons or keys provided on the case of the ophthalmologic apparatus 1 or its outside. For example, if the retinal camera unit 2 has a case that is the similar to conventional retinal cameras, a joy stick, operation panel, etc. provided on this case may be included in the operation part 242. Furthermore, the display 241 may include various display devices such as a touch panel, etc. provided on the case of the retinal camera unit 2.

It should be noted that the display 241 and the operation part 242 do not need to be configured as separate devices. For example, like a touch panel, a device in which the display function and the operation function are integrated can be used. In such cases, the operation part 242 is configured to include this touch panel and a computer program. The content of operation via the operation part 242 is input to the controller 210 as an electric signal. Moreover, operations and inputs of information may be performed by using a graphical user interface (GUI) displayed on the display 241 and the operation part 242.

OPERATIONS

Operations of the ophthalmologic apparatus 1 are described below.

Operation Example 1

Figure 6:
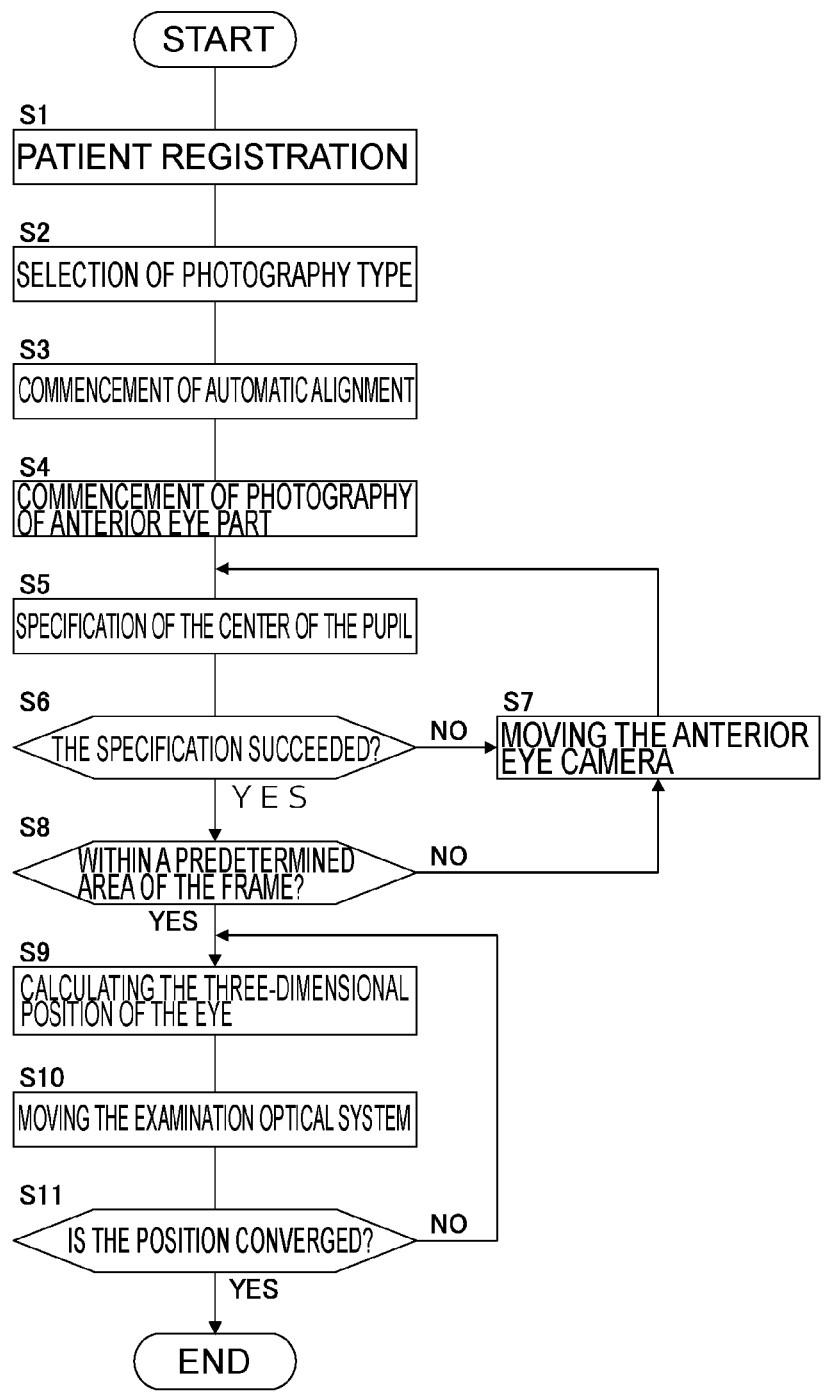
FIG. 6 is a flowchart showing an operational example of an ophthalmologic apparatus according to an embodiment.

This operation example describes a whole process of a series of actions including automatic alignment. Now, the flowchart shown in FIG. 6 is referred to.

(S1: Patient Registration)

First, the user inputs patient information on a subject using the user interface 240. The patient information may be a patient ID, patient name, etc.

(S2: Selection of Photography Type)

Next, the user uses the user interface 240 to select and input the type of photography carried out with respect to the subject. The items of the photography type may include, for example, a photographing site (optic papilla, macula, or both, etc.), the photographed eye (left eye, right eye, both eyes), image photographing pattern (only a fundus image, only an OCT image, or both), OCT scanning pattern (line scan, cross scan, radial scan, circle scan, three-dimensional scan, etc.)

(S3: Commencement of Automatic Alignment)

Once the selection of the photography type is completed, an instruction for commencing automatic alignment is given. This commencement instruction may be automatically given by the controller 210 upon receiving the selection of the photography type or may be manually given by the user using the operation part 242.

(S4: Commencement of Photography of Anterior Eye Part)

Once the instruction for commencing automatic alignment is given, the controller 210 causes the respective anterior eye cameras 300A and 300B to commence photographing of the anterior eye part Ea. This photographing is moving image photography of the anterior eye part Ea as the photography subject. The respective anterior eye cameras 300A and 300B carry out moving image photography at a predetermined frame rate. Here, the timings of photographing by the anterior eye cameras 300A and 300B may be synchronized by the controller 210. The respective anterior eye cameras 300A and 300B successively transmit the acquired frames to the controller 210 in real time. The controller 210 associates the frames obtained by both anterior eye cameras 300A and 300B in accordance with the photography timing. That is, the controller 210 associates the frames substantially simultaneously acquired by both anterior eye cameras 300A and 300B with each other. This association is carried out based on, for example, the abovementioned synchronous control or based on the input timings of the frames from the anterior eye cameras 300A and 300B. The controller 210 transmits the pair of the associated frames to the analyzer 231.

(S5: Specification of the Center of the Pupil)

The image correction part 2311 corrects the distortion of each frame transmitted from the controller 210 based on the aberration information 212a stored in the storage 212. This correcting process is carried out in the abovementioned manner. The pair of frames with the distortion thereof corrected is transmitted to the characteristic position specifying part 2312.

The characteristic position specifying part 2312 analyzes each frame transmitted from the image correction part 2311, thereby carrying out the process for specifying the characteristic position in the frame corresponding to the center of the pupil of the anterior eye part Ea.

(S6: Has the Specification of the Center of the Pupil Succeeded?)

In the event of failure in specifying the characteristic position corresponding to the center of the pupil (S6: NO), the characteristic position specifying part 2312 transmits the information indicating this result to the controller 210, and the process is transferred to "Moving the anterior eye camera" of Step S7. On the other hand, if specification of the center of the pupil has been successful (S6: YES), it shifts to "Is the image of the anterior eye part positioned within a predetermined area of the frame?" of Step S8.

(S7: Moving the Anterior Eye Camera)

In the event of failure in specifying the characteristic position (S6: NO), the controller 210, in response to reception of the information from the characteristic position specifying part 2312, controls the camera moving part mentioned above to move the anterior eye cameras 300A and 300B in the direction away from the supporter 440 and/or the direction outwards of the supporter 440.

In the event of moving the anterior eye cameras 300A and 300B in the direction away from the supporter 440, the distance between the anterior eye cameras 300A and 300B and the subject (the eye E) increases; thereby, it becomes possible to photograph a wider scope of the subject's face, increasing the possibility of the eye E being positioned in a range suitable for photographing by the anterior eye cameras 300A and 300B. Moreover, in the event of moving the anterior eye cameras 300A and 300B in the direction outwards of the supporter 440, the anterior eye cameras 300A and 300B move in the direction of the subject's ear, increasing the possibility of the eye E being positioned in a range suitable for photographing by the anterior eye cameras 300A and 300B. Moreover, by combining the movement in these two directions, the possibility of the eye E being positioned in a range suitable for photographing is further enhanced.

In this operation example, it is regarded that the moving image photography of the anterior eye part Ea is continued even while moving or after moving the anterior eye cameras 300A and 300B. Instead, it is possible to stop the moving image photography upon moving the anterior eye cameras 300A and 300B and automatically or manually re-starting the moving image photography after the moving is completed.

After completion of moving the anterior eye cameras 300A and 300B, moving image photography by the anterior eye cameras 300A and 300B, specification of the center of the pupil, and determination for successful specification are carried out again. It should be noted that a configuration is possible of transferring to manual alignment when this routine is repeated a predetermined number of times.

(S8: Is the Image of the Anterior Eye Part Positioned within a Predetermined Area of the Frame?)

Upon successful specification of the characteristic position corresponding to the center of the pupil (S6: YES), the image determination part 232 determines whether or not the image corresponding to the anterior eye part Ea is within a predetermined area of the frame. In this operation example, this determination process is carried out using the characteristic position specified by the characteristic position specifying part 2312. Instead, when using other information to carry out the determination process, the abovementioned processes may be in any order.

In the event a determination is made that the image of the anterior eye part Ea is not positioned within a predetermined area of the frame (S8: NO), the anterior eye cameras 300A and 300B are moved again (S7). On the other hand, in the event a determination is made that the image of the anterior eye part Ea is positioned within a predetermined area of the frame (S8: YES), it goes to "Calculating the three-dimensional position of the eye" of the next step (S9).

(S9: Calculating the Three-Dimensional Position of the Eye)

The three-dimensional position calculating part 2313 calculates the three-dimensional position of the center of the pupil of the eye E based on the positions of the anterior eye cameras 300A and 300B and the characteristic position specified by the characteristic position specifying part 2312 regarding the pair of frames. This process is carried out in the abovementioned manner.

(S10: Moving the Examination Optical System)

Based on the three-dimensional position of the center of the pupil calculated by the three-dimensional position calculating part 2313 in Step S9, the controller 210 controls the optical system driver 2A so as to match the optical axis of the examination optical system with the axis of the eye E, and such that the distance of the examination optical system with respect to the eye E becomes the specific working distance.

(S11: Is the Position Converged?)

When the examination optical system is moved, the controller 210 determines whether or not the position of the examination optical system has converged. This determination process is carried out by, for example, using the alignment target. The observation condition of the alignment target changes depending on the alignment state. Specifically, when the alignment is in a suitable state, two images of the alignment target are observed in substantially the same position, while the more the alignment state worsen, the more the two images are observed apart from each other. The controller 210 obtains the distance between these two images photographed by the CCD image sensor 35, and determines whether or not this distance is within a specific threshold or less. When a determination is made that the distance is equal to the specific threshold or less, it is determined that the position of the examination optical system is converged, completing the process (S11: YES).

Whereas, when a determination is made that this distance exceeds the specific threshold, it is determined that the position of the examination optical system is not converged, returning to the process "Calculating the three-dimensional position of the eye" of Step 9 (S11: NO). The processes from "Calculating the three-dimensional position of the eye" of Step 9 to Step 11 are repeated until, for example, determined as "NO" in Step 11 a specific number of times. In the event the determination of "NO" is repeated the specific number of times, the controller 210 outputs, for example, a specific warning information. Moreover, in correspondence with the determination of "NO" being repeated the specific number of times, the controller 210 may execute control of transferring to an operation mode for carrying out manual alignment or an operation mode for automatic alignment using the alignment target.

It should be noted that such position convergence determination process is not limited to this; however, any method is possible as long as the process is capable of determining whether or not the position of the examination optical system is appropriately converged. This concludes the explanation of the automatic alignment according to this operation example.

Operation Example 2

This operation example explains the operation of the ophthalmologic apparatus 1 applicable when there is a danger of the eye having a negative influence on light irradiated onto the fundus, such as the case in which the eye has a cataract. Moreover, this operation example explains a new alignment method and a new method of representing alignment state regarding an ophthalmologic apparatus.

The automatic alignment explained in Operation example 1 above involves automatically carrying out alignment with respect to the center of the pupil of the eye; however, when the crystalline lens is opaque, for example, due to cataracts, signal light becomes scattered by the opaque portion, thereby preventing effective OCT images from being acquired. Under such conditions, in this operation example, alignment is performed with respect to the position dislocated from the center of the pupil, thereby carrying out OCT measurement by avoiding the opaque portion.

Figure 7A:
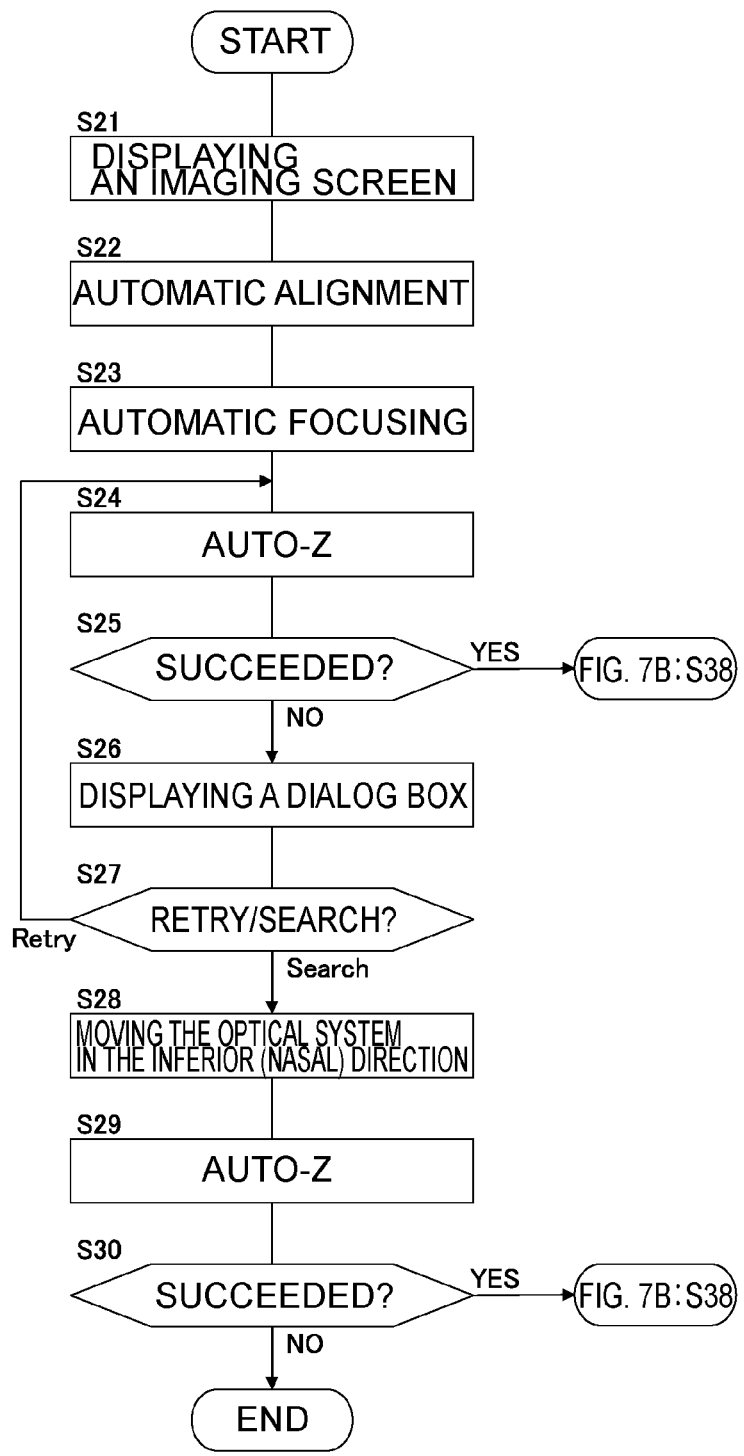
FIG. 7A is a flowchart showing an operational example of an ophthalmologic apparatus according to an embodiment.
Figure 7B:
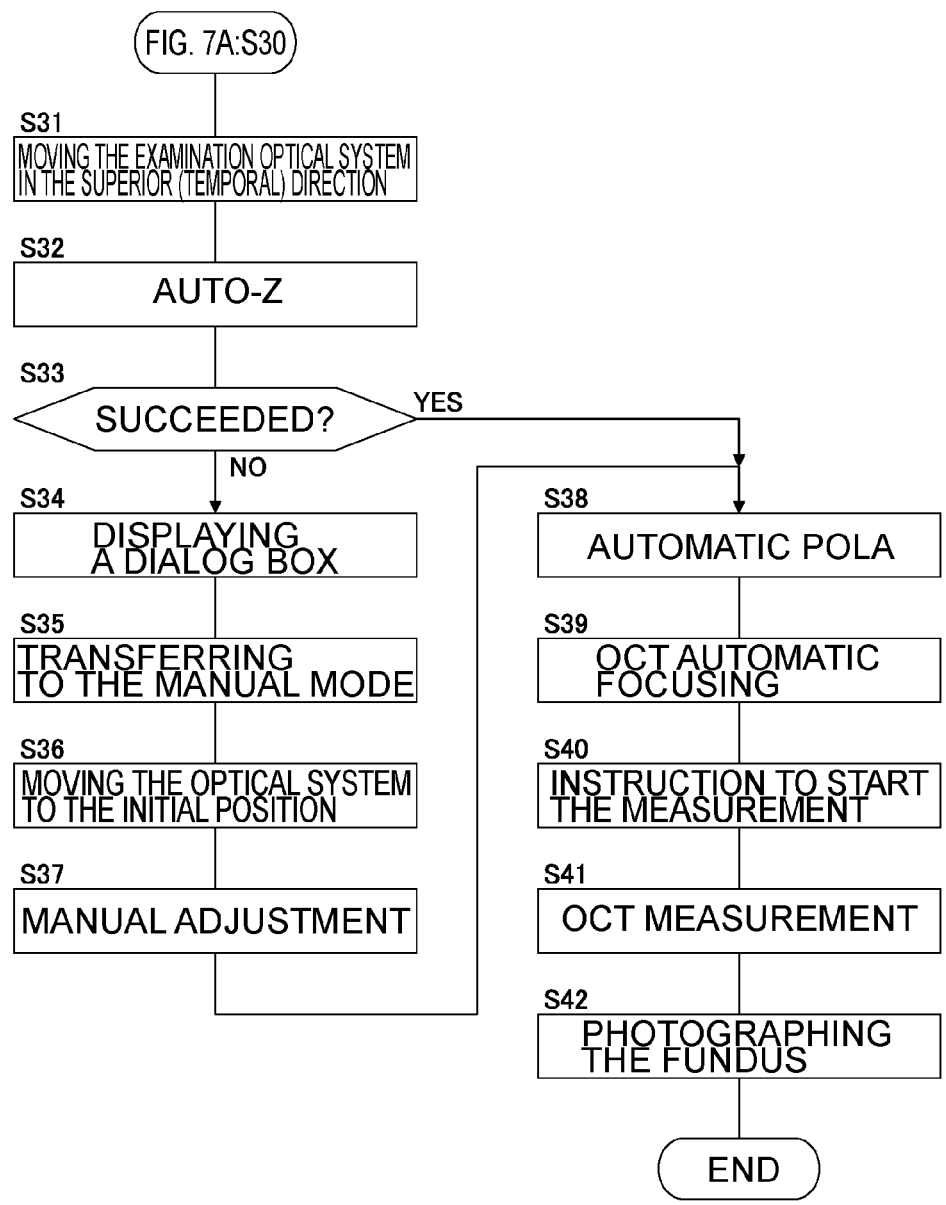
FIG. 7B is a flowchart showing an operational example of an ophthalmologic apparatus according to an embodiment.

An example of a process flow of this operation example is shown in FIG. 7A and FIG. 7B. Further, examples of displayed screens in this operation example are shown in FIG. 8A to FIG. 8I. Here, it is assumed that the patient registration (S1) and the selection of the photography type (S2) in Operation example 1 have already been carried out, and that the imaging by the anterior eye cameras 300 has already been started (S4).

(S21: Displaying an Imaging Screen)

The controller 210 controls the display 241 to display an imaging screen 1000 shown in FIG. 8A. In the display region (first display region) 1001 on the left hand side in the imaging screen 1000, an infrared observation image (a front image of the anterior eye part Ea) 2000 acquired by the retinal camera unit 2 is displayed in real time as a moving image. Further, in the display region (second display region) 1002 on the right hand side in the imaging screen 1000, an anterior eye image acquired by one of the anterior eye cameras 300A and 300B is displayed as a moving image. A "Capture START" button 1003 is provided below the second display region.

(S22: Automatic Alignment)

Upon receiving the operation (click operation) to the "Capture START" button 1003, the controller 210 controls the display 241 to display an alignment screen 1010 for executing automatic alignment (see FIG. 8B). At least an image used for carrying out the automatic alignment is displayed in the alignment screen 1010.

The automatic alignment is carried out, for example, in the manner as explained in Operation example 1. Alternatively, it is also possible to carry out the automatic alignment based on a pair of anterior eye images acquired by the anterior eye cameras 300A and 300B.

An example of the automatic alignment using a pair of anterior eye images acquired by the anterior eye cameras 300A and 300B is explained. In the present example, two anterior eye images of the eye E acquired by the anterior eye cameras 300A and 300B are synthetically displayed. These anterior eye images are respectively acquired in real time, and the synthetic image (composed image) of them is displayed as a moving image in real time. That is, this synthetic display is a moving image display in which a synthetic image (still image) based on the two anterior eye images (still images) substantially simultaneously acquired by the anterior eye cameras 300A and 300B is regarded as a single frame.

A method or creating each frame (each synthetic image) is explained. As mentioned above, a single frame is based on the anterior eye images substantially simultaneously acquired by the anterior eye cameras 300A and 300B.

As the first example of forming a frame, it is possible to display a partial image of one anterior eye image and a partial image of another anterior eye image in parallel. For these partial images, parts differing from each other are used in the original frames. Each of the partial images is obtained by trimming part of its original anterior eye image. This process is carried out by the controller 210 or the image processor 230.

A first display region 1011 and a second display region 1012 are provided in the alignment screen 1010 shown in FIG. 8B. In the first display region 1011, a first partial image 2110 corresponding to the upper half of the frame of the anterior eye image acquired by the anterior eye camera 300A is displayed. In the second display region 1012, a second partial image 2120 corresponding to the bottom half of the frame of the anterior eye image acquired by the eye camera 300B is displayed. The first display region 1011 and the second display region 1012 are arranged such that the former is in the upper position and the latter is in the lower position. Here, the lower side of the first display region 1011 and the upper side of the second display region 1012 are in contact. In this manner, two partial images are displayed such that they are arranged in accordance with their positional relationship in the present example.

When the retinal camera unit 2 is moved in the ±z-direction by the optical system driver 2A, along with the change in positions of the anterior eye cameras 300A and 300B with respect to the eye E, the two partial images 2110 and 2120 are relatively and transversely displaced each other. Moreover, when the retinal camera unit 2 is moved in the xy-direction by the optical system driver 2A, along with the change in positions of the anterior eye cameras 300A and 300B with respect to the eye E, the two partial images 2110 and 2120 are integrally displaced within the respective display regions 1011 and 1012 in a direction in accordance with the moving direction of the optical system of the apparatus.

As explained above, the analyzer 231 analyzes the first partial image 2110 (or the whole original image thereof) to specify the image region corresponding to the characteristic site of the eye E (first characteristic region). Similarly, the analyzer 231 analyzes the second partial image 2120 (or the whole original image thereof) to specify the image region corresponding to the characteristic site of the eye E (second characteristic region). Each of the characteristic sites is, for example, a pupil (the outline of the pupil or the center of the pupil). In FIG. 8B, the symbol 2110a indicates a first characteristic region corresponding to the outline of the pupil, and the symbol 2120a indicates a second characteristic region corresponding to the outline of the pupil.

Moreover, the analyzer 231 calculates the displacement between the first characteristic region 2110a and the second characteristic region 2120a. This displacement includes the displacement in the lateral direction. As described above, the lateral displacement corresponds to the positional gap of the examination optical system in the ±z-direction. The analyzer 231 obtains the moving direction and the moving distance of the examination optical system that correspond to the displacement between the first characteristic region 2110a and the second characteristic region 2120a calculated by itself. This process is carried out by, for example, referring to information associating displacements between characteristic regions with moving directions and moving distances. This information is created in advance based on the locations of the two anterior eye cameras 300A and 300B and/or working distance, and stored in the storage 212 or the analyzer 231.

The controller 210 controls the optical system driver 2A based on the moving direction and the moving distance obtained by the analyzer 231 to move the retinal camera unit 2 in the +z-direction or −z-direction. By performing such processes, alignment in the z-direction is carried out such that the first characteristic region 2110a and the second characteristic region 2120a match each other (that is, the combination of the first characteristic region 2110a and the second characteristic region 2120a forms an image depicting the pupil) (see FIG. 8C).

The parenthesis 2101 represented in substantially the center of the screen and the circle 2102 surrounded by this parenthesis illustrated in FIG. 8C indicates the target position for alignment. The parenthesis 2101 shows a target position of the outline of the pupil, and the circle 2102 shows a target position of the center of the pupil.

Further, the analyzer 231 calculates the displacement of the respective positions of the first characteristic region 2110a and the second characteristic region 2120a and the target position (the parenthesis 2101, the circle 2102). Moreover, the analyzer 231 derives the moving direction and the moving distance of the examination optical system corresponding to the displacement calculated by itself. This process is carried out by, for example, referring to information associating displacements between characteristic regions and target positions with moving directions and moving distances. This information is created in advance based on the locations of the two anterior eye cameras 300A and 300B and/or working distance, and stored in the storage 212 or the analyzer 231.

The controller 210 controls the optical system driver 2A based on the moving direction and the moving distance obtained by the analyzer 231 to move the retinal camera unit 2 in the +x-direction or −x-direction and/or in the +y-direction or −y-direction. By performing such processes, alignment in the xy-direction is carried out. By adjusting both the alignment state in the xy-direction and the alignment state in the z-direction, the examination optical system is located in the suitable three-dimensional position with respect to the eye E. At this time, the alignment screen 1010 is in the display state illustrated in FIG. 8C.

As a second example of preparing a frame, at least part of one anterior eye image may be overlaid on at least part of the other anterior eye image. This overlay is carried out by using, for example, a layering function. The opacity (the alpha channels of the pixels) of the front layer is set beforehand to a specific value allowing visual contact of the image on the rear layer. This process is carried out by the controller 210. In the present example as well, the alignment screen 1010 illustrated in FIGS. 8B and 8C is displayed, and alignment in the z direction and alignment in the xy-direction are carried out in the same manner as the first example. The displacement of the images regarding these alignments is also the same as in the first example.

The "Capture STOP" button 1013 shown in FIG. 8B and FIG. 8C is operated (clicked) for stopping (or suspending) the process of this operation example.

(S23: Automatic Focusing)

Upon receiving the completion of the automatic alignment, the controller 210 carries out automatic focusing using the split target in the way described above.

(S23: Automatic Focus)

Upon receiving the completion of the automatic focusing, the controller 210 controls the display 241 to display the Auto-Z screen 1020 shown in FIG. 8D, and starts Auto-Z. It should be noted that the configuration is also possible in which Auto-Z is started in response to prescribed trigger (for example, the instruction by the user).

(S24: Auto-Z)

In the Auto-Z screen 1020, the synthetic image (an image obtained by composing two anterior eye images) 2130 similar to that in the alignment screen 1010 of FIG. 8C is displayed. The display mode of this synthetic image 2130 is, for example, movie display; however, it may be a still image display. The synthetic image 2130 is, for example, displayed in the upper right region of the Auto-Z screen 1020.

The OCT image display part 1021 for displaying OCT images is provided below the synthetic image 2130. Further, the indicator 1022 for representing prescribed evaluation value is provided below the OCT image display part 1021. This evaluation value may be a value indicating the image quality of the image displayed in the OCT image display part 1021, or a value indicating the degree of success/failure of Auto-Z (e.g. a value calculated based on the distance between the image corresponding to a prescribed tissue of the eye E and a target area in the frame). The evaluation value is calculated by, for example, the analyzer 231 analyzing an OCT image (cross sectional image). The controller 210 displays the calculated evaluation value in the indicator 1022.

The front image 3000 of the fundus Ef is displayed on the left of the synthetic image 2130 and the OCT image display part 1021. The front image 3000 may be an infrared observation image, an infrared photographed image, or a color image. The infrared observation image is a real time moving image obtained by photographing the fundus Ef. The infrared photographed image and the color image are still images photographed the fundus Ef in the past. It should be noted that it is also possible to display a moving image obtained in the past as the front image 3000. The front image 3000 is overlaid by the arrow mark indicating a scanning position applied in OCT measurement. At least part of this mark may indicate a scanning position applied in Auto-Z. The user can arbitrarily change the position of the mark by using the operation part 242. The controller 210 is capable of control the galvano scanner 42 so as to perform scanning based on the position of the mark after the change.

(S25: Succeeded?)

When Auto-Z has succeeded in this stage (S25: YES), Step S38 of FIG. 7B is carried out. Step S38 and the processes after this are described later.

(S26: Displaying a Dialog Box)

On the other hand, when Auto-Z has failed (S25: NO), the controller 210 displays the dialog box 1030 as a pop-up display shown in FIG. 8E. The dialog box 1030 is provided with a message "Could not detect image" indicating the failure of Auto-Z and software keys 1031 and 1032. The software key 1031 is a "Retry" button, and the software key 1032 is a "Search" button.

(S27: Retry/Search?)

When the "Retry" button 1031 is operated (clicked) (S27: Retry), the process is returned to Step S24 and Auto-Z is started again.

(S28: Moving the Optical System in the Inferior (Nasal) Direction)

On the other hand, when the "Search" button 1032 is operated (clicked) (S27: Search), the controller 210 controls the optical system driver 2A to move the retinal camera unit 2 in the predetermined direction by predetermined distance. Thereby, the position of the examination optical system relative to the eye E is changed in the predetermined direction by predetermined distance.

Further, the controller 210 displays a dialog box indicating the movement state of the examination optical system as a pop-up display. The dialog box 1040 shown in FIG. 8F is an example of the dialog box displayed when the examination optical system is moved to lower position.

The movement direction of the examination optical system is set in the direction perpendicular to the OCT scanning direction in Auto-Z. This is based on the fact that when the examination optical system is moved in the scanning direction, the optical path length of the signal light in the eye, thereby the position of the image of the eye depicted in the frame is shifted in the vertical direction.

Figure 9A:
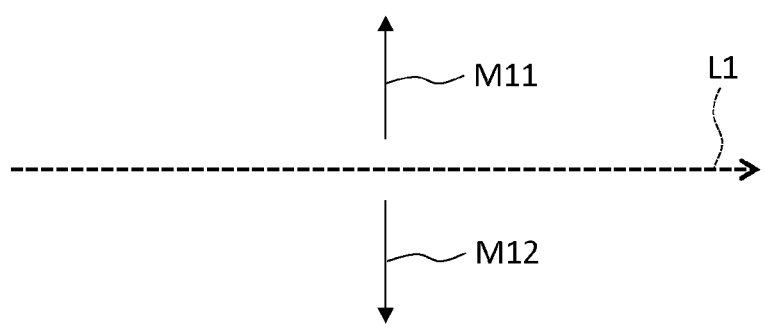
FIG. 9A is a schematic diagram for explaining an operational example of an ophthalmologic apparatus according to an embodiment.
Figure 9B:
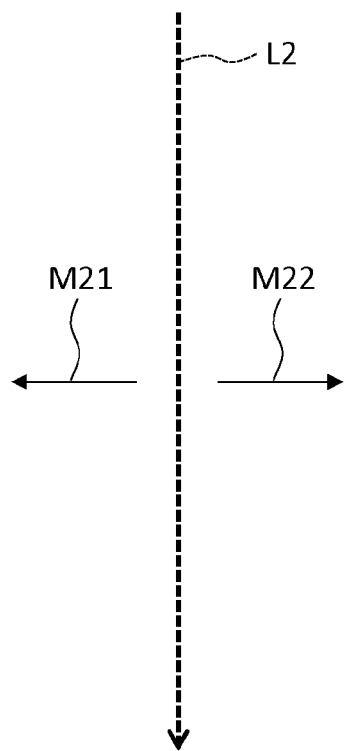
FIG. 9B is a schematic diagram for explaining an operational example of an ophthalmologic apparatus according to an embodiment.

Examples of the movement direction of the examination optical system are illustrated in FIG. 9A and FIG. 9B. As shown in FIG. 9A, when the horizontal line scanning (horizontal scanning) L1 is applied in Auto-Z, it is possible to move the examination optical system in the direction perpendicular to the horizontal scanning L1 (that is, the upward direction M11 or the downward direction M12) in Step S28.

It should be noted that when the subject is an aged person, the upper eyelid is nutated and positioned just in front of the pupil. Considering such situation, when the horizontal scanning L1 is applied in Auto-Z, it is to be desired that the examination optical system is moved in the downward direction M12.

Further, when the vertical line scanning (vertical scanning) L2 is applied in Auto-Z as shown in FIG. 9B, it is possible to move the examination optical system in the direction perpendicular to the vertical scanning L2 (that is, the leftward direction M21 or the rightward direction M22) in Step S28.

When the eye E is a left eye, the leftward direction M21 corresponds to the ear side, and the rightward direction M22 corresponds to the nose side. On the other hand, when the eye E is a right eye, the leftward direction M21 corresponds to the nose side, and the rightward direction M22 corresponds to the ear side. In general, the directions in the fundus Ef is expressed by the upward direction (superior), the downward (inferior), the nose side (nasal), and the ear side (temporal). Here, vertical direction is set along the midline (sagittal line) of the subject, the "nasal" corresponds to the direction getting closer to the sagittal line along the direction perpendicular to the sagittal line, and the "temporal" corresponds the direction getting going away from the sagittal line along the direction perpendicular to the sagittal line. That is, the line indicating the superior-inferior direction and the line indicating the nasal-temporal direction are perpendicular to each other.

In this operation example, when the vertical scanning L2 is applied in Auto-Z, the examination optical system is controlled to move in the nasal direction. It should be noted that the movement direction of the examination optical system in this stage may be arbitrary (that is, may be the superior direction, the temporal direction, or an oblique direction).

FIG. 10 illustrates an example of the movement direction of the examination optical system in the case in which various scanning patterns can be applied. Here, "3D" indicates three-dimensional scan, "Radial" indicates radial scan, and "Line" indicates line scan. Further, "5LineCross" indicates a scan pattern combining five parallel line scans in vertical direction and five parallel line scans in horizontal direction. Moreover, "Macula" indicates that the imaging target is a macula, while "Disc" indicates that the imaging target is an optic papilla. Moreover, "Wide" refers to scanning a wide range, while "H" indicates the horizontal direction and "V" indicates the vertical direction. The information illustrated in FIG. 10 is stored in the storage 212 in advance. The controller 210 may obtain the movement direction corresponding to the scanning pattern applied, and control the optical system driver 2A so as to move the examination optical system in the movement direction obtained.

Figure 11:
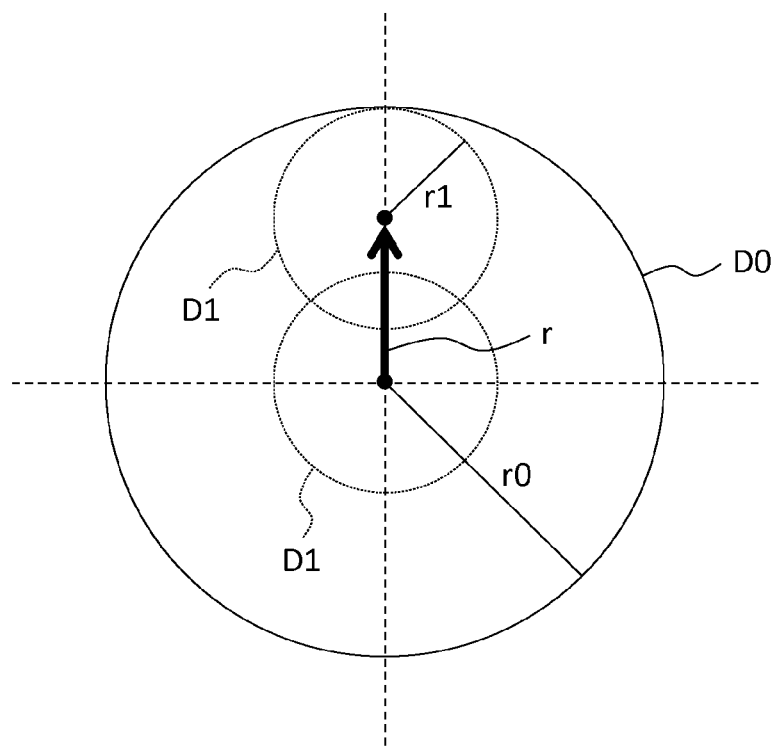
FIG. 11 is a schematic diagram for explaining an operational example of an ophthalmologic apparatus according to an embodiment.

Next, the movement distance of the examination optical system is explained. The movement distance is, for example, as indicated in FIG. 11, determined from the diameter of the minimal pupil region DO to which OCT measurement can be applied (minimum pupil diameter) "2*r0" (for example, 2.5 mm), and the diameter of the beam cross-section D1 of the signal light (beam diameter) "2*r1" (for example, 1.1 mm). The maximum movement distance is the half of the difference between the minimum pupil diameter and the beam diameter: r=r0−r1. It should be noted that the movement distance of the examination optical system in Step S28 may be the maximum movement distance calculated in this manner (0.7 mm), or may be shorter distance. That is, the movement distance of the examination optical system may be arbitrary set within a range in which signal light is not irradiated to the iris that shaping the pupil. For example, it is possible to stepwise move the alignment position in this range.

(S29: Auto-Z)

In response to the completion of the movement of the examination optical system, the controller 210 carries out Auto-Z again.

(S30: Succeeded?)

When Auto-Z has succeeded in this stage (S30: YES), Step S38 of FIG. 7B is carried out. Step S38 and the processes after this are described later. On the other hand, when Auto-Z has failed in this stage (S30: NO), Step S31 of FIG. 7B is carried out.

(S31: Moving the Examination Optical System in the Superior (Temporal) Direction)

When Auto-Z has failed in Step S30 (S30: NO), the controller 210 controls the optical system driver 2A to move the retinal camera unit 2 in the opposite direction to that in Step S28. For example, when the examination optical system is moved in the inferior (or nasal) direction in Step S28, the examination optical system is moved in the superior (or temporal) direction in Step S31.

Further, the movement distance in Step S31 is set, for example, the double of the movement distance in Step S28. In this case, the optical axis of the examination optical system is moved to the position predetermined distance (e.g. 0.7 mm) away from the initial position (the center of the pupil) in the inferior (or nasal) direction in Step S28, and then, moved to the position predetermined distance (e.g. 0.7 mm) away from the initial position in the superior (or temporal) direction in Step S31.

Further, the controller 210 displays a dialog box indicating the movement state of the examination optical system as a pop-up display. The dialog box 1050 shown in FIG. 8G is an example of the dialog box displayed when the examination optical system is moved to upper position.

(S32: Auto-Z)

In response to the completion of the movement of the examination optical system, the controller 210 carries out Auto-Z again.

(S33: Succeeded?)

When Auto-Z has succeeded in this stage (S33: YES), Step S38 of FIG. 7B is carried out. Step S38 and the processes after this are described later.

(S34: Displaying a Dialog Box)

When Auto-Z has failed in Step S33 (S33: NO), the controller 210 displays the dialog box 1060 shown in FIG. 8H as a pop-up display. The dialog box 1060 is provided with a message "Could not detect image. Search image manually" indicating the failure of (the final) Auto-Z and prompting to transfer manual adjustment. Further, the dialog box 1060 is provided with the "OK" button 1061.

(S35: Transferring to the Manual Mode)

Figure 8H:
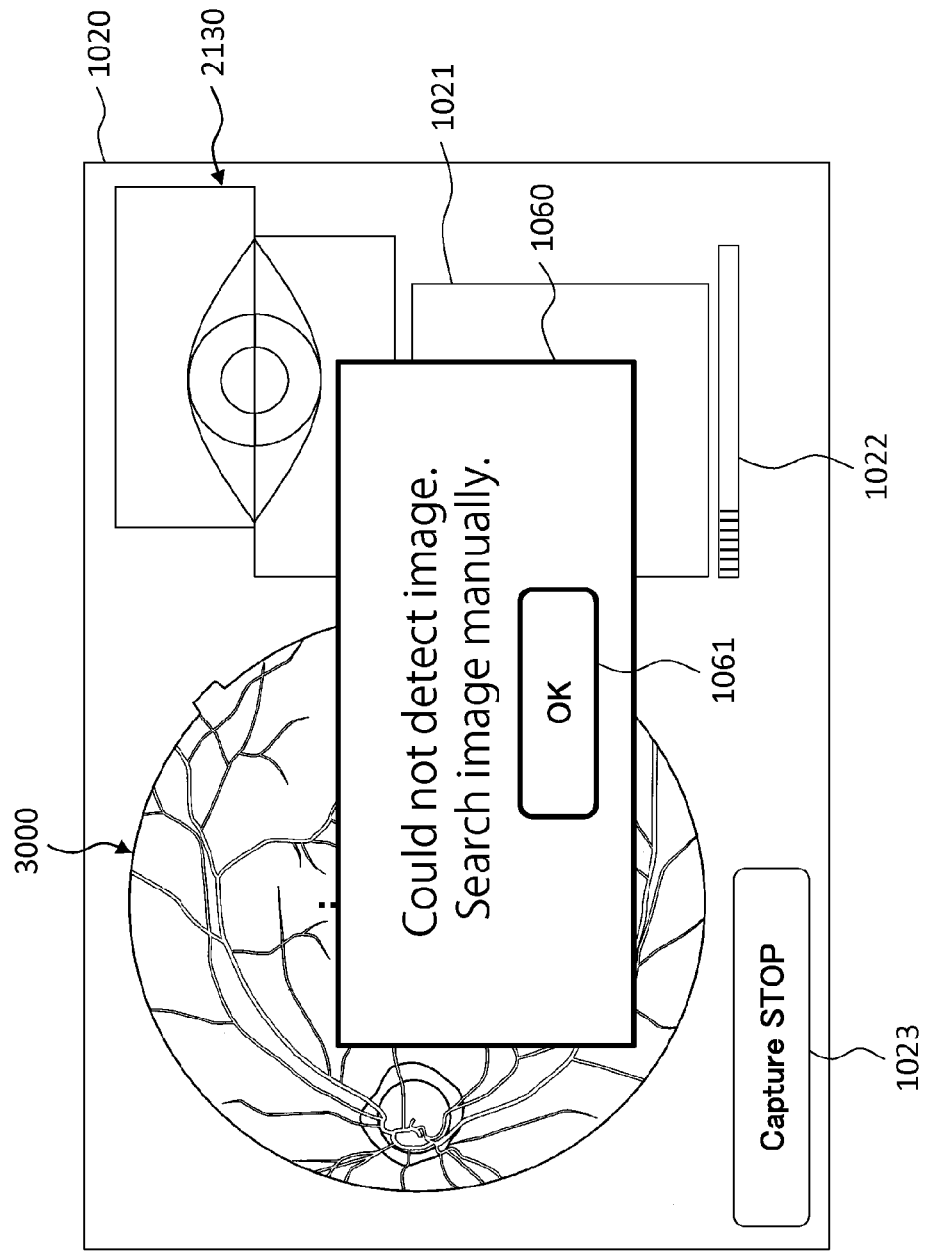
FIG. 8H is a schematic diagram showing an example of a screen displayed by an ophthalmologic apparatus according to an embodiment.
Figure 8I:
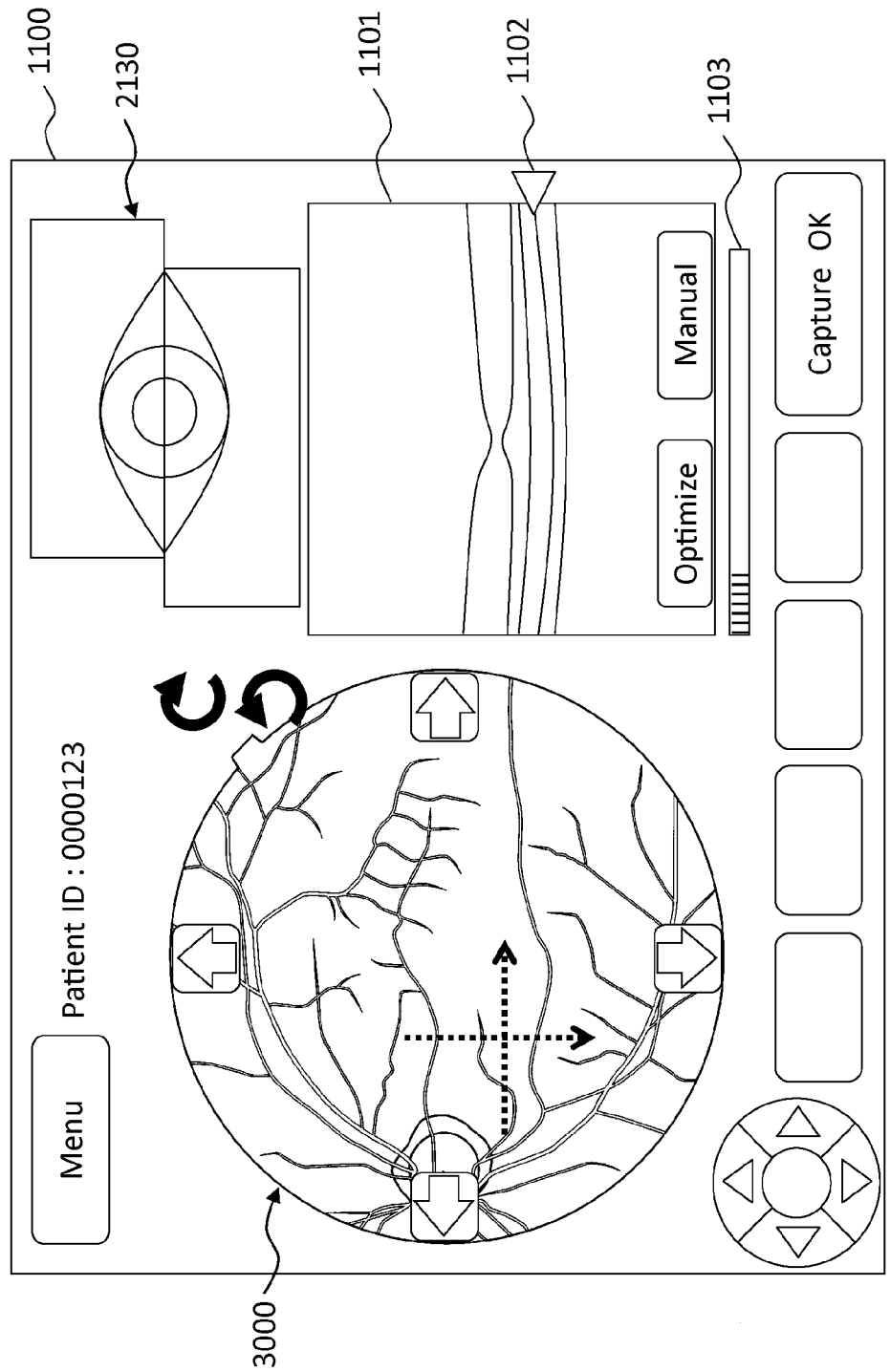
FIG. 8I is a schematic diagram showing an example of a screen displayed by an ophthalmologic apparatus according to an embodiment.

Upon receiving the operation of the "OK" button 1061, the controller 210 displays the manual mode screen 1100 shown in FIG. 8I. The manual mode screen 1100 is used for manual alignment, and for manually performing processes to depict the image of the fundus Ef within the target area in the frame.

Images and software keys for carrying out the above processes are represented in the manual mode screen 1100. Specifically, the synthetic image 2130 of the anterior eye part Ea and the front image 3000 of the fundus Ef are displayed in the manual mode screen 1100. Further, the manual mode screen 1100 is provided with the OCT image display part 1101. OCT images acquired in real time and/or OCT images acquired in the past are displayed in the OCT image display part 1101. The measurement depth marker 1102 is provided in the right end part of the OCT image display part 1101. The measurement depth marker 1102 is described later.

The indicator 1103 for presenting a predetermined evaluation value is provided below the OCT image display part

1101. The evaluation value represents the image quality of the image displayed in the OCT image display part 1101, and it is calculated by the analyzer 231 analyzing an OCT image (cross sectional image). The controller 210 displays the evaluation value calculated in the indicator 1103.

An example of the operation mode using the manual mode screen 1100. The arrow buttons for moving the acquiring position of the front image two-dimensionally is provided in the upper end, the lower end, the left end and the right end of the front image 3000. When any one of the arrow buttons is operated, the controller 210 controls the optical system driver 2A to move the examination optical system in the direction (xy-direction) corresponding to this arrow button. Further, alignment in the z-direction is carried out by using a software key or a hardware key (illustration omitted) (the operation part 242). More specifically, when the user operates this software key or a hardware key, the controller 210 controls the optical system driver 2A based on the operation content thereof to move the examination optical system in the +z-direction or the −z-direction. The movement of the examination optical system causes change of the relative position of the respective anterior eye cameras 300 in relation to the eye E. As a result, the position of the image of the anterior eye part Ea depicted in the synthetic image 2130 (depicted position in the frame) is changed. The user carries out movement operation of the examination optical system, while referring to the synthetic image 2130, such that the characteristic part (pupil region etc.) of the anterior eye part Ea is positioned at the position of the target (illustration omitted) displayed over the synthetic image 2130.

An arrow mark indicating the scanning position of the signal light is displayed over the front image 3000. The user moves the mark by operating the arrow buttons, thereby being capable of arbitrarily change the scanning position. The movement of the scanning position is reflected to the control of the galvano scanner 42.

A pair of rotation buttons (arc-shaped arrow mark) is provided in the upper right position of the front image 3000. The user operates these rotation buttons to arbitrarily rotate the scanning position. The rotation of the scanning position is reflected to the control of the galvano scanner 42.

The measurement depth marker 1102 arranged in the right end part of the OCT image display part 1101 is moved in the vertical direction by click operations and/or drag operations using the operation part 242. The controller 210 carries out control of the optical-path-length changing part 41 in accordance with the position of the measurement depth marker 1102. Thereby, the measurement depth of OCT is changed. In other words, the depiction position of the image of the fundus Ef in the frame is moved in the z-direction.

The "Optimize" button for automatically carrying out the image quality optimization and the "Manual" button for manually carrying out the image quality optimization are provided in the OCT image display part 1101. The image quality optimization includes a process for adjusting the difference of the optical path length of the signal light and the optical path length of the reference light.

Software keys for carrying out various operations are provided in the lower left part of the front image 3000. The software keys are used for moving the internal fixation target projected by LCD 39 to a default position and moving the projection position of the internal fixation target in the vertical and horizontal directions.

Further, for example, the following software keys are provided in the manual mode screen 1100: software keys for moving the examination optical system in the front-back direction (the z-direction), the horizontal direction (x-direction) and the vertical direction (y-direction); software keys for carrying out focus adjustment; software keys for changing the types of the fixation target; software keys for turning on/off an external fixation target (illustration omitted); software keys for change the operation mode to the microcoria mode (that is, for inserting a microcoria diaphragm in the optical path).

(S36: Moving the Optical System to the Initial Position)

In response to transition to the manual mode, the controller 210 controls the optical system driver 2A to move the examination optical system to the initial position. The initial position is the position of the examination optical system before Step S28, and specifically, it corresponds to the position in which the examination optical system is matched with the center of the pupil, which is achieved by the automatic alignment (S22). The processes in Step S36 may include any of the following; (1) the examination optical system is return to the position obtained in Step S22; (2) new automatic alignment is carried out.

(S37: Manual Adjustment)

The user performs alignment, focusing, and a process for depicting the image of the fundus Ef within the target area in the frame. After completing the manual adjustment, the user operates (clicks) the "Capture OK" button provided in the lower right part of the manual mode screen 1100.

(S38: Automatic Pola)

When Auto-Z in Step S24 has succeeded (S25: NO), when Auto-Z in Step S29 has succeeded (S30: NO), when Auto-Z in Step S32 has succeeded (S33: NO), or when the "Capture OK" button is operated in Step S37, the controller 210 carries out automatic polarization adjustment (automatic Pola). The automatic Pola is carried out by, for example, controlling the polarization adjuster 106 while evaluating, in real time, the image quality of OCT images (cross sectional images) repeatedly acquired.

(S39: OCT Automatic Focusing)

After the completion of automatic Pola, the controller 210 carries out OCT automatic focusing. The OCT automatic focusing is a process to change the optical path length of the signal light by controlling the optical-path-length changing part 41 so as to optimize the interference sensitivity of the signal corresponding to a prescribed site of the fundus Ef (for example, any layer of the retina, or choroid).

(S40: Instruction to Start the Measurement)

After the completion of OCT automatic focusing, the controller 210 controls the display 241 to display information showing this fact (illustration omitted). The user performs a trigger operation for starting the measurement of the fundus Ef by using the operation part 242.

It is also possible to apply a configuration in which the completion of OCT automatic focusing is used as the trigger for starting the measurement. In this case, Step S40 is not necessary.

(S41: OCT Measurement)

Upon receiving the trigger for starting the measurement, the controller 210 causes the OCT unit 100 to carry out the OCT measurement of the fundus Ef. The image forming part 220 forms an OCT image based on the detection signals from the OCT unit 100. The controller 210 stores the OCT image formed in the storage 212. When three-dimensional scan is applied, the image processor 230 forms three-dimensional image data based on multiple cross sectional images formed by the image forming part 220. The controller 210 stores the three-dimensional image data formed in the storage 212.

(S42: Photographing the Fundus)

Upon receiving the completion of the OCT measurement, the controller 210 causes the retinal camera unit 2 to photograph the fundus Ef. The image data obtained by the retinal camera unit 2 is stored in the storage 212 by the controller 210. This is the end of the explanation of this operation example.

Operation Example 3

This operation example explains a technology that is capable of preferably acquiring front images of an eye fundus even though the subject eye is a microcoria (small pupil) eye. In the above-mentioned operational example 2, the front image 3000 of the fundus Ef is displayed on the Auto-Z screen 1020 and the manual mode screen 1100 (see FIG. 8D to FIG. 8I). The front image 3000 is a moving image or a still image acquired by the retinal camera unit 2 (or by an external apparatus such as a retinal camera or scanning laser ophthalmoscope (SLO)), and are specifically an infrared observation image, infrared photographed image or color photographed image. As mentioned above, when the eye E is a microcoria eye, there are cases in which fundus imaging is not preferably performed by using the retinal camera unit 2.

In order to solve such a problem, the present operational example explains an example for displaying a front image acquired by OCT measurement of the fundus Ef. More specifically, a front image (OCT front image) of the fundus Ef acquired by OCT measurement is displayed over an infrared observation image (infrared front image) acquired by an retinal camera function or SLO function in the present operational example. It should be noted that since the present embodiment is configured to acquire these two front images by coaxial optical systems, position matching between the front images is unnecessary or easy.

The OCT front image is acquired in real time, and the display mode thereof is movie display. On the other hand, the infrared front image may be acquired in real time or have been acquired in the past. The display mode in the former case may be movie display or still image display. The display mode in the latter case is still image display, for example. When the infrared front image is displayed as a still image, it is possible to perform position matching between the infrared front image and the OCT front image in real time. This position matching may be performed so as to coincide the positions of characteristic sites in these images with each other, for example. More specifically, this position matching may include: a process for specifying the characteristic site (optic papilla, macula, blood vessel, lesion site, etc.) within each of the images; a process for calculating the displacement between the characteristic site in the infrared front image and the characteristic site in the OCT front image; and a process for relatively shifting the infrared front image and the OCT front image (for example, affine transformation) such that the calculated displacement is cancelled.

Figure 12:
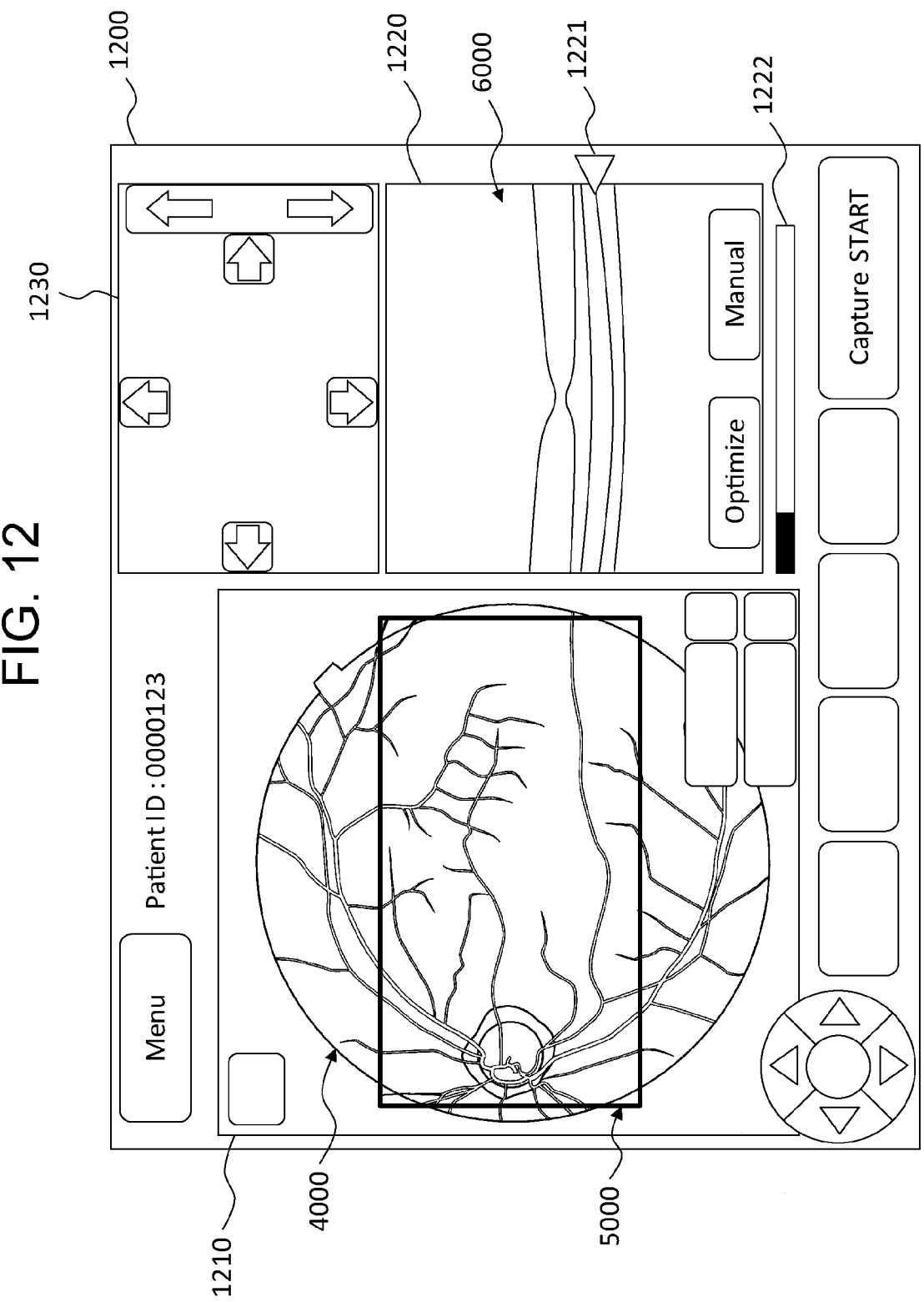
FIG. 12 is a schematic diagram illustrating an example of a screen displayed by an ophthalmologic apparatus according to an embodiment.

FIG. 12 illustrates an example of composite display of the infrared front image and the OCT front image obtained in such a way. The display screen 1200 shown in FIG. 12 is provided with a front image display part 1210, tomographic image display part 1220, and image display part 1230. The composite image of the infrared front image and the OCT front image (xy cross sectional image) is displayed in the front image display part 1210. The tomographic image 6000 of the fundus Ef is displayed in the tomographic image display part 1220. The tomographic image 6000 is an OCT image depicting a cross section in the different direction from the cross section of the OCT front image (that is, xy cross section), and is, for example, an xz cross sectional image or a yz cross sectional image. In the image display part 1230, an arbitrary image of the eye E is displayed as necessary. Examples of images displayed in the image display part 1230 include a photographed image of the fundus Ef, an observation image or photographed image of anterior eye part Ea, an anterior eye image acquired by the anterior eye camera(s) 300.

The composite image displayed in the front image display part 1210 is explained. The infrared front image is, for example, an observation image (real-time infrared moving image) of the fundus Ef obtained by the retinal camera unit 2. It should be noted that the infrared front image may be an image (moving or still image) obtained by the retinal camera unit 2 or other apparatus (SLO, for example) in the past; however, the present example explains the case in which a real-time infrared moving image is used. When the eye E is a microcoria eye, the infrared front image is darker and more unclear than the case in which the eye E is not a microcoria eye.

The OCT front image is generated from data set obtained by three-dimensional scan of the fundus Ef (volume data, stack data, 3D interferogram, for example). In the present operational example, time-series data sets are obtained in real time by repeatedly executing three-dimensional scan, and an OCT front image is generated, as a real-time moving image, based on the time-series data sets.

Examples of a process for generating a frame of the OCT front image from data set (volume data, stack data, 3D interferogram, etc.) at each time point included in the time-series data sets are explained. The first process example includes a process of adding up (or integrating) the values of the picture elements (voxel values or pixel values) in the volume data (or the stack data) in the depth direction (z-direction). The image generated by this process is called a projection image etc.

The second process example includes a process of adding up (or integrating) the values of the picture elements (voxel values or pixel values) in partial data of the volume data (or the stack data) in the depth direction (z-direction). The partial data corresponds to a portion of the volume data between a first depth position and a second depth position. Here, the first and second depth positions may correspond to sites of the fundus Ef or to the z-coordinate of the volume data. The image generated by this process is called a shadowgram etc.

The third process example is explained. In the present example, the OCT front image is generated from 3D interferogram acquired by the OCT unit 100. That is, the OCT front image is generated without processing image data such as volume data or stack data.

A general Fourier domain OCT interferogram equation is given by the expression:

$$G_d(v) = G_s(v)\left\{1 + \sum_n R_n + 2\sum_{n \neq m} \sqrt{R_n R_m} \cos[2\pi v(\tau_n - \tau_m)] + 2\sum_n \sqrt{R_n} \cos[2\pi v(\tau_n - \tau_r)]\right\}$$

wherein v is the frequency of the beam of light; $R_n$ and $R_m$ are the intensity reflections at particular xy-plane locations n and m, respectively, from an object (eye); $G_s(v)$ is the spectral density of light source; the reflection of the reference arm (reference optical path) is unity; and distances are represented by propagation times $\tau_n$ and $\tau_m$ in signal optical path and $\tau_r$ in reference optical path. The third term in brackets on the right hand side is the mutual interference for all light scattered within the object and the last term contains the interference between the scattered light from the object and the reference light, from which an A-scan (i.e., axial length scan) is calculated.

In the case of spectral domain OCT, the parameter v represents a position on a line sensor (line scan camera). As such, the first two terms may represent slow variation across a linear array of camera pixels while the last two terms may represent oscillations (i.e., interference fringes). Similarly, when the light source is a tunable swept-source and is swept through a range of frequencies v, the first two terms in the primary equation represent slow variation in time of the detected signal, while the last two terms represent oscillations.

In the present operational example, high-pass filtering will eliminate all but the third and fourth terms on the right side of the equation and, given that the magnitude of the fourth term is typically much larger than the third when an object with low reflectivity is present along the signal optical path, will effectively isolate the fourth term. Further, a range, deviation, standard deviation, variance, or entropy of the high-pass filtered spectra may be used to generate a two-dimensional image intensity map of the object.

Figure 13:
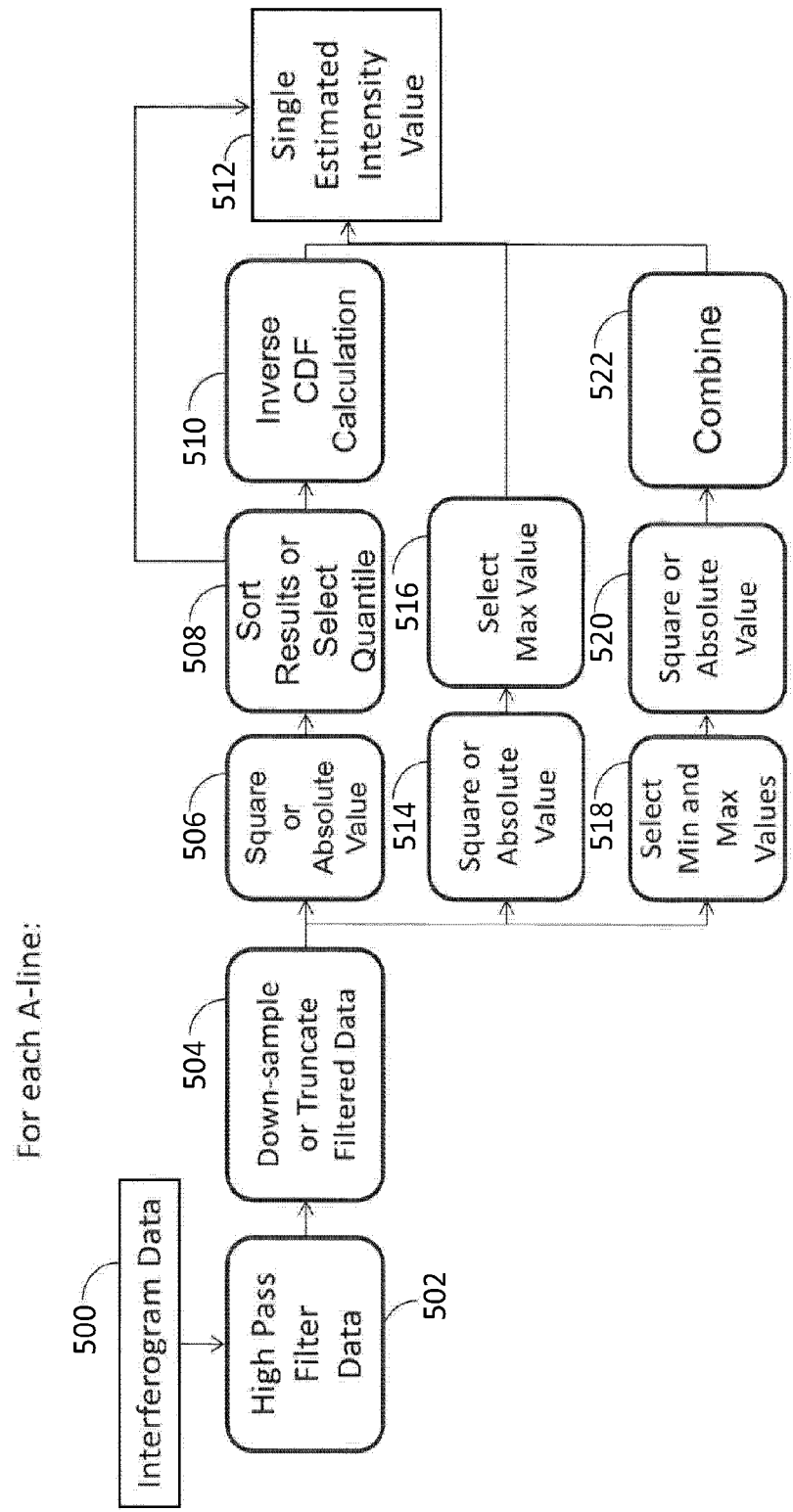
FIG. 13 is a schematic diagram for explaining an operational example of an ophthalmologic apparatus according to an embodiment.

FIG. 13 illustrates a workflow diagram for processing OCT interferogram data in the present operational example. The methodology illustrated in FIG. 13 includes estimating and quantifying a distribution of high-pass filtered interferogram data to determine one or more single estimated intensity values corresponding to one or more xy-plane locations over the object. For example, interferogram data (e.g., a plurality of sets of outputs) is received from the OCT unit 100 at 500. The interferogram data may be high-pass filtered at 502 to simplify the terms of the Fourier domain interferogram equation by effectively isolating the fourth term as described above. In one example, the data rate or size of the high-pass filtered interferogram data may be further reduced through various known down-sampling or truncation techniques at 504 to, for example, allow for greater processing efficiency or faster calculations. Alternatively, the data may be truncated or down-sampled prior to the high-pass filtering of the interferogram data. For example, the interferogram data (either before or after) high-pass filtering may be down-sampled by retaining every nth output and discarding all others. In another example, the interferogram data may be truncated by retaining data within a selected range while discarding all other data.

The set of filtered outputs may then be translated into a single estimated intensity value in the depth direction Z for the particular X-Y plane location based on an inverse cumulative distribution function (CDF). In general, a CDF function describes the probability that a real-valued random variable x with a given probability distribution will be found at a value less than or equal to x. The inverse CDF, also known as a quantile function, of a random variable specifies, for a given probability, the value which the variable will be at or below, with that probability.

Alternatively, the inverse CDF may be a quick-select or Hoare's selection function, wherein it is generally not necessary to sort the entire set of filtered outputs. Rather, only a portion of the set of filtered outputs, e.g., sub-arrays around pivot values that include a desired quantile selection, is actually sorted.

In another alternative, the inverse CDF or quantile function may employ a set of heuristics operable to estimate a quantile value without having to sort the set of filtered outputs.

Returning to the first inverse CDF approach, the set of filtered outputs may be squared at 506 (i.e., for positive and negative values to exist in the same realm) and sorted at 508 for an inverse CDF function at 510. In the present operational example, the set of filtered outputs may be sorted in either ascending or descending order at 508 to determine a value corresponding to an arbitrary percentile that may be selected for the inverse CDF calculation. For example, a 0th percentile may correspond to a minimum percentile value and minimum filtered output value, a 50th percentile may correspond to a median percentile value and median filtered output value, and a 100th percentile may correspond to a maximum percentile value and maximum filtered output value. Therefore, if there are 2048 filtered outputs and a 90th percentile is selected, the 1843rd sorted value is the selected value. In one example, the at least one selected percentile value may correspond to a value between a $50^{th}$ and a $100^{th}$ percentile value. However, the at least one selected percentile value may correspond to any pre-selected percentile value within the set of filtered outputs. As such, once a sorted value corresponding to an arbitrary percentile is selected, the sorted value may be translated into the single estimated intensity value at 512.

In a variation of the first inverse CDF approach, a set of heuristics may be employed at 508 that are operable to estimate a quantile value without having to sort the set of filtered outputs. The estimated value then may be translated into the single estimated intensity value at 512.

In alternative examples, maximum and minimum based approaches that are conceptually similar to the inverse CDF approach may be employed to determine a single estimated intensity value. In maximum and minimum based approaches, the set of filtered outputs do not need to be sorted to generate single estimated intensity values. For example, a maximum percentile based approach generally corresponds to the inverse CDF approach when a 100th percentile is selected. In one example, the square or the absolute value of the filtered outputs may be determined at 514 to eliminate the possibility of negative values, and a maximum ($100^{th}$) percentile value determined from these results at 516 may represent a single estimated intensity value 512. In a maximum and minimum based approach, the maximum and minimum percentile values are determined at 518, and the square or the absolute value of the maximum and minimum percentile values may be determined to eliminate the possibility of negative values at 520. The resulting values then may be combined at 522 to determine a single estimated intensity value 512. For example, combination operations may include taking the minimum, maximum, or average of the two resulting values. Moreover, the scale of the single estimated intensity value 512 may be further translated by, for example, taking the logarithm or a root (e.g., square, cubic, fourth) of the generated value. Furthermore, a minimum and maximum based approach may be generalized such that the top n minimum and top n maximum values are determined in block 518. In this generalized example, the combination operation of 522 could consist of taking an average of the 2n values or taking a pre-selected percentile value using the inverse CDF methodology. One or more single estimated intensity values corresponding to one or more xy-plane locations (i.e., multiple A-lines) may be suitable for generating a two-dimensional image intensity map of the object.

By applying the above-mentioned process to interferogram data for respective A-lines acquired from three-dimensional scan of the fundus Ef, a two-dimensional intensity map, that is, an OCT front image of the fundus Ef is generated. An estimated intensity value calculated by the above process is assigned to each pixel of the OCT front image obtained in such a way.

Processes for compositely displaying an infrared front image and OCT front image are explained. FIG. 14 illustrates the infrared front image 4000 and FIG. 15 illustrates the OCT front image 5000. As explained above, the infrared front image 4000 is a moving image or a still image of the fundus Ef acquired by the retinal camera unit 2 or other apparatus. it should be noted that a color image etc. may be used instead of the infrared front image 4000.

The OCT front image 5000 is obtained by executing three-dimensional scan using the OCT function of the ophthalmologic apparatus 1. The OCT front image 5000 is, for example, a projection image or shadowgram of volume data or stack data obtained from three-dimensional scan (the first or second process example explained above), or a two-dimensional intensity map generated by applying the third process example to interferogram data for multiple A-lines obtained from three-dimensional scan.

It should be noted that the OCT front image 5000 is a single frame successively acquired in real time by repeatedly carrying out three-dimensional scan in the present operational example. The controller 210 synthesizes and displays each of successively acquired frames (OCT front image 5000) and the infrared front image 4000. It should be noted that in the case in which the infrared front image 4000 is also a moving image, the controller 210 may synthesizes and displays a single frame (still image) of this moving image and the OCT front image 5000, or may associate the infrared front image 4000 with the OCT front image 5000, each of which is a frame of a moving image, and synthesizes and displays them. In the latter case, the association may be carried out as follows. When the infrared front image 4000 is also a real-time moving image, the controller 210 associates frames of the infrared front image 4000 and the OCT front image 5000, wherein the frames have been acquired at substantially the same timing. This simultaneity is, for example, based on input timings of image signals (video signals) into the controller 210. Alternatively, it may utilize a configuration in which the imaging rate of the retinal camera unit 2 and the scan rate of the OCT function are synchronized in advance. When the infrared front image 4000 is a moving image acquired in the past, frames of the infrared front image 4000 and frames of the OCT front image 5000 may be arbitrarily associated.

Figure 14A:
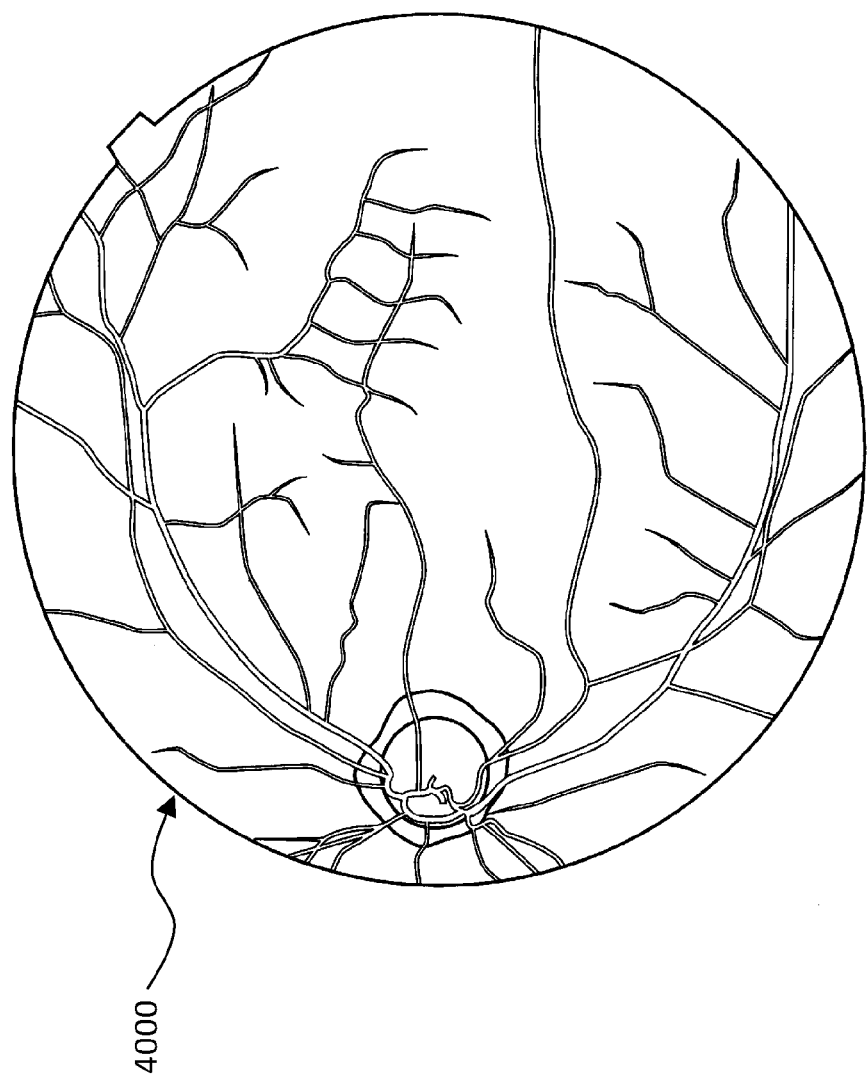
FIG. 14A is a schematic diagram for explaining an operational example of an ophthalmologic apparatus according to an embodiment.
Figure 14B:
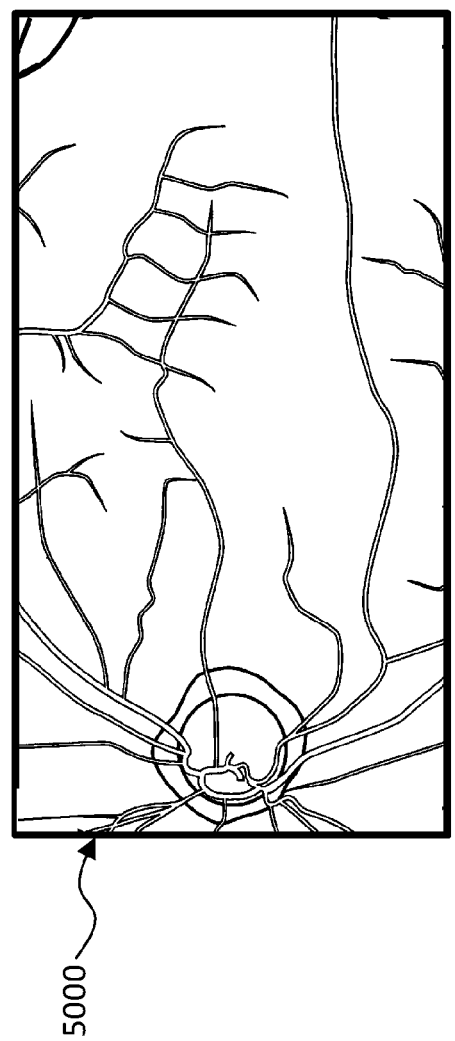
FIG. 14B is a schematic diagram for explaining an operational example of an ophthalmologic apparatus according to an embodiment.
Figure 15:
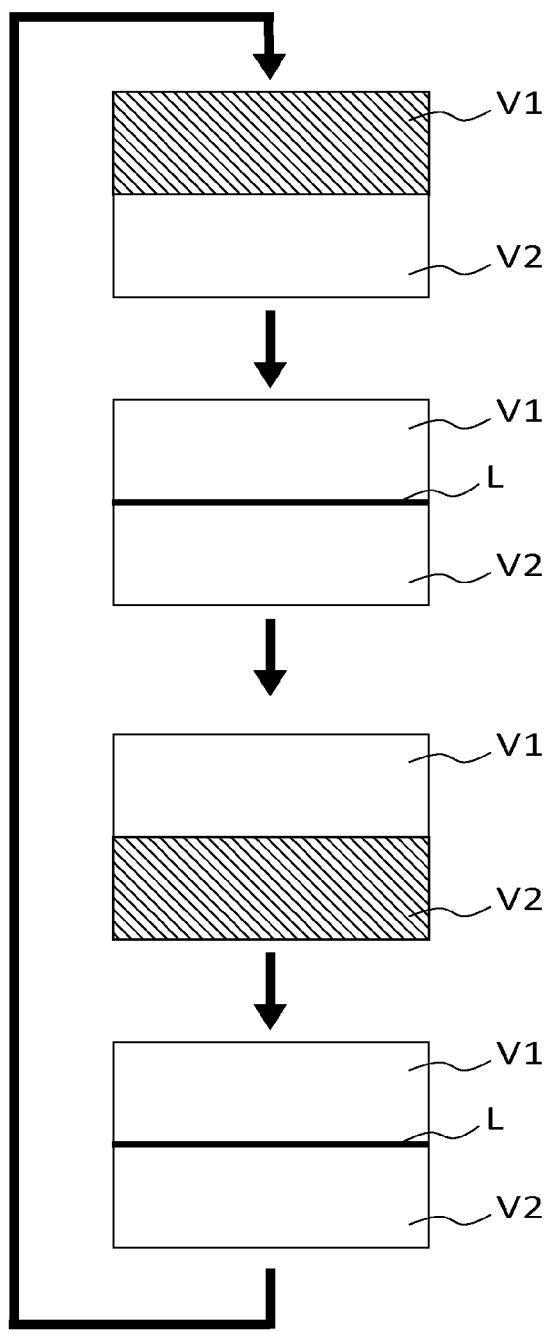
FIG. 15 is a schematic diagram for explaining an operational example of an ophthalmologic apparatus according to an embodiment.

As shown in FIG. 14A to FIG. 14C, the imaging area of the infrared front image 4000 (first imaging area) and the imaging area of the OCT front image 5000 (second imaging area) are overlapped in the present operational example. The overlapped areas are arbitrary set. Specifically, the first imaging area may be contained in the second imaging area; the second imaging area may be contained in the first imaging area; a part of the first imaging area and a part of the second imaging area may be overlapped. It should be noted that in the example shown in FIG. 14A to FIG. 14C, a part of the imaging area of the infrared front image 4000 and a part of the imaging area of the OCT front image 5000 are overlapped.

The compose display process of the infrared front image 4000 and the OCT front image 5000 may include position matching for these images. This position matching process has been explained above. It should be noted that in the ophthalmologic apparatus 1 according to the present embodiment, the optical system for acquiring the infrared front image 4000 (the imaging optical system 30) and the optical system for acquiring the OCT front image 5000 (the optical system that forms optical path of the signal light LS) are coaxially arranged through the dichroic mirror 46 (see FIG. 1). Therefore, in the case in which the infrared front image 4000 and the OCT front image 5000 are both real-time moving images, the position matching is not necessary. It should be noted that adjustment of the sizes of both images may be carried out. This adjustment process is, for example, carried out by affine transformation similar to the position matching process. Even when these optical systems are not coaxial, it is possible to calculate the displacement between the images from the relative position between the optical axes of these optical systems in advance, and to carry out the position matching between the infrared front image 4000 and the OCT front image 5000 so as to cancel the displacement.

The composite display of the infrared front image 4000 and the OCT front image 5000 is overlaying display, for example. This process is carried out by using layer function, for example. Specifically, the infrared front image 4000 is displayed on a back layer the OCT front image 5000 is displayed on a front layer. The opacity (alpha value of pixels) of the front layer is arbitrary. For example, in the case in which the eye E is a microcoria eye and the brightness of the infrared front image 4000 is not enough, the front layer may be set to be opaque. In this case, the whole of the OCT front image 5000 and the partial region of the infrared front image 4000 which does not correspond to the imaging area of the OCT front image 5000 are presented.

In addition to the infrared front image 4000 and the OCT front image 5000, other information may be compositely displayed. Examples of such information include the alignment target and the split target. In the case in which the infrared front image 4000 is a real-time moving image and the target is projected onto the eye E, a target image is depicted in the infrared front image 4000. In this case, the controller 210, for example, sets the front layer to be semitransparent, thereby presenting the target image depicted on the back layer. Alternatively, the configuration is possible in which the image processor 230 specifies the position of the target image in the infrared front image 4000 and the controller 210 displays a mark (a mark of the same shape as the target image, for example) at the location on the OCT front image 5000 corresponding to the position specified by the image processor 230.

The configuration according to the present operational example is effective for the case in which the eye E is a microcoria eye. Specifically, in the case in which an ophthalmologic apparatus has a retinal camera function and an OCT function, and an infrared front image can be acquire in real time by using the retinal camera function, it is not necessary to display the OCT front image when the eye E is not a microcoria eye and sufficiently clear infrared front images can be acquired. Based on such considerations, the following configuration may be employed.

The ophthalmologic apparatus 1 comprises a means (information obtaining part) configured to obtain information showing the pupil size of the eye E. the information showing the pupil size may be numerical information representing the pupil size (e.g. pupil diameter) of the eye E, or information showing whether or not the eye E is a microcoria eye. When the numerical information is obtained, the controller 210 compares the pupil size with predetermined threshold to judge whether the eye E is a microcoria eye or not. The information obtaining part may include the user interface 240 or the controller 210 (communication interface etc.) the user interface 240 is used for manually inputting information showing the pupil size. As a concrete example, the display 241 is received control from the controller 210 and displays screen for inputting information. The user operates the operation part 242 to input information showing the pupil size into the screen. When the information obtaining part includes the communication interface, the controller 210 obtains information showing the pupil size of the eye E that is stored in an external apparatus (electronic medical record server in the medical institution, for example) via a network. Alternative example of the information obtaining part is a reader configured to read information recorded in a recording medium. As another example, the ophthalmologic apparatus 1 may measure the pupil size by analyzing an anterior eye image of the eye E. In this case, the combination of the function for imaging an anterior eye (the retinal camera unit 2 or the anterior eye camera(s) 300) and the image processor 230 corresponds to the information obtaining part.

The controller 210 selectively execute, based on the information obtained by the information obtaining part, a display mode (first display mode) in which the infrared front image 4000 and the OCT front image 5000 are compositely displayed and a display mode (second display mode) in which the infrared front image 4000 is displayed. Specifically, the controller 210 executes the first display mode when the eye E is a microcoria eye, and executes the second display mode when the eye E is not a microcoria eye.

An operational example is explained in which the composite image of the infrared front image 4000 and the OCT front image 5000 are displayed as a movie and a tomographic image is displayed in the tomographic image display part 1220 as a movie. The controller 210 controls the galvano scanner 42 and the OCT unit 100 to execute, in alternate fashion, a first scan mode (three-dimensional scan) in which the irradiation position of the signal light LS on the fundus is two-dimensionally changed and a second scan mode in which the irradiation position of the signal light LS on the fundus is one-dimensionally changed. It should be noted that examples of the second scan mode include line scan, circle scan, etc.; however the case in which the line scan is employed is explained below.

The switching of the first and second scan modes is carried out at preset timings. For example, it is possible to alternately execute m times of three-dimensional scans for a preset region and n times of line scans for a preset region (here, each of m and n is an integer equal to or larger than 1).

As an alternative example, in the case in which a preset region for three-dimensional scan is divided into k subregions V1 to Vk (here, k is an integer larger than 1), the scanning may be executed in the following order: three-dimensional scan for the subregion V1; line scan; three-dimensional scan for the subregion V2; line scan; . . . ; three-dimensional scan for the subregion Vk; line scan; three-dimensional scan for the subregion V1; line scan; . . . . That is, while executing three-dimensional scans for the subregions V1 to Vk in a cyclic fashion, line scan is executed between the three-dimensional scan for the subregion Vi and the three-dimensional scan for the subregion V(i+1). An example of such control is illustrated in FIG. 15. In this example, a region for three-dimensional scan is divided into two rectangular subregions V1 and V2. The symbol L shows the boundary line of the first subregion V1 and the second subregion V2. The controller 210 carries out control for repeatedly executing a series of scans, wherein the series of scans consists of the three-dimensional scan for the subregion V1, the line scan for the boundary line L, the three-dimensional scan for the subregion V2, and the line scan for the boundary line L.

A process for forming OCT images in the case in which the controller 210 carries out, in an alternate fashion, the first scan mode (three-dimensional scan) and the second scan mode (line scan). It should be noted that parallel to such scanning control, infrared moving image capturing is carried out by the retinal camera unit 2.

The controller 210 receives video signals acquired by the infrared moving image capturing and alternately receives detection signals acquired by three-dimensional scan and detection signals acquired by line scan.

The detection signals acquired by three-dimensional scan are used for forming the OCT front image 5000. The image formation process is carried out by the image forming part 220 and the image processor 230 when the OCT front image 5000 is a projection image or a shadowgram, and it is carried out by the image processor 230 when the OCT front image 5000 is formed from interferogram data.

The detection signals acquired by line scan are used for forming a two-dimensional tomographic image whose cross section lies along the scanning line (the boundary line L, for example) and the z-direction. The image formation process is carried out by the image forming part 220.

Therefore, the ophthalmologic apparatus 1 of the present example acquires the OCT front image 5000 (moving image) and the tomographic image (moving image) by alternately executing three-dimensional scan and line scan while acquiring the infrared front image 4000 by carrying out infrared moving image capturing of the fundus Ef. The controller 210 executes control for displaying (as a movie) the OCT front image 5000 over the infrared front image 4000 in an overlay fashion and control for displaying the tomographic image 6000 as a movie in the tomographic image display part 1220 in parallel. Thereby, the display mode illustrated in FIG. 12 is realized.

When such a display mode is carried out, the following processes may be additionally executed. A first process example stops update of frames of moving image while the eye E is blinking. A second process example sets a region for three-dimensional scan based on a position having been set for line scan (or circle scan etc.). A third process example changes the size of a region for three-dimensional scan in accordance with sites of the eye E to be imaged. A fourth process example changes the density of three-dimensional scan in accordance with sites of the eye E to be imaged. A fifth process example executes three-dimensional scan and line scan with different scan densities.

The first process example is explained. Since OCT measurement and infrared moving image capturing cannot be carried out while the eye E is blinking, frames obtained during blinking period are not inappropriate. The present process example stops updating frames while the eye E is blinking to avoid displaying an inappropriate moving image.

A configuration for realizing the present process example is explained. The ophthalmologic apparatus 1 is provided with a function for detecting a blink of the eye E (blink detecting part). The blink detecting part includes the controller 210 or the image processor 230, for example. The controller 210 or the image processor 230, for example, analyzes frames of the infrared front image 4000, interferogram data acquired by OCT measurement, or image data generated from the interferogram to judge whether the eye E is blinking or not. This judgment process uses the fact that data acquired when the eye E is blinking and data acquired by scanning the fundus Ef are different from each other. For example, interferogram data acquired by scanning the fundus Ef includes information corresponding to layers in the fundus Ef although data acquired during blinking does not include such information. The controller 210 or the image processor 230 determines whether such information is included or not based on the waveform of the interferogram data, for example. As another example, the judgment whether or not the eye E is blinking may be carried out by comparing data previously acquired and data newly acquired. For example, every time new interferogram data is acquired, the controller 210 or the image processor 230 compares this new interferogram data and the interferogram data acquired immediately before, and judges that the eye E is blinking when the difference obtained from the comparison is no less than a preset threshold.

In response to the detection of blinking by the blink detecting part, the controller 210 stop updating frames for at least one of the infrared front image 4000, the OCT front image 5000 and the tomographic image 6000. Further, in response to the fact that blinking is no longer detected by the blink detecting part when the frames are not being updated, the controller 210 resumes the update of frames. According to such a configuration, the latest appropriately acquired frame is continuously displayed during the eye E blinking.

The second process example is explained. In fundus observation, there is a demand for observing a cross section of a specific site while observing the surrounding thereof. In order to satisfy the demand, the ophthalmologic apparatus 1 may present the tomographic image 6000 depicting the site the user wants to observe the most while presenting the OCT front image 5000 (and the infrared front image 4000) depicting the surrounding thereof. The present process example may be carried out such that the acquisition area of the OCT front image 5000 is automatically set in accordance with the acquisition position of the tomographic image 6000.

A configuration for realizing the present process example is explained. The ophthalmologic apparatus 1 is provided with a function for setting a one-dimensional scan region (the boundary line L, for example) for line scan (setting part). The setting part comprises the user interface 240, for example. As a specific example, the display 241 receives control from the controller 210 and displays the infrared front image 4000. The user operates the operation part 242 to designate a position in the infrared front image 4000. This designated position corresponds to the one-dimensional region. As another example, when the site for line scan (macula, optic papilla, etc.) is set in advance, a configuration may be employed in which the infrared front image 4000 is analyzed by the image processor 230 to specify an image region corresponding to this site, and a cross section for line scan is set such that the cross section passes the specified image region.

The controller 210 controls the galvano scanner 42 and the OCT unit 100 so as to scan a two-dimensional region in which the one-dimensional scan region set by the setting part is located in the center by the signal light LS, thereby executing three-dimensional scan.

Here, the region for line scan is a one-dimensional region on the surface of the fundus Ef, and is a two-dimensional region in the real space and the three-dimensional image space. Similarly, the region for three-dimensional scan is a two-dimensional region on the surface of the fundus Ef, and is a three-dimensional region in the real space and the three-dimensional image space. The expression that the above one-dimensional scan region is located in the center of the above two-dimensional region means that the above one-dimensional scan region passes through the center position of the above two-dimensional region. For example, in the example shown in FIG. 15, the boundary line L (the above one-dimensional scan region) is set so as to pass through the center of the composite region (the above two-dimensional region) of the subregions V1 and V2.

It should be noted that the positional relationship between the region for line scan and the region for three-dimensional scan is not limited to this. That is, the region for line scan may be located at an arbitrary position in the region for three-dimensional scan. For example, when line scan of the macula and three-dimensional scan of area containing the macula and the optic papilla are carried out, the region for line scan is set at a position shifted from the center of the region for three-dimensional scan. Further, at least part of the region for line scan is not necessarily located in the region for three-dimensional scan.

The third process example is explained. As mentioned before, in fundus observation, there is a demand for observing a cross section of a specific site while observing the surrounding thereof. The specific site is an optic papilla or a macula, for example. Further, there are cases in which the area of the surrounding region to be observed is changed in accordance with the specific sites. For example, the area of the surrounding region in the case of observing a cross section of the optic papilla may be smaller than the area of the surrounding region in the case of observing a cross section of the macula. The present process example automatically changes the area for three-dimensional scan in accordance with the site to which line scan is applied.

A configuration for realizing the present process example is explained. The site to which line scan is applied is changed by the selection of fixation positions of the eye E. The ophthalmologic apparatus 1 is provided with a fixation optical system. Once a fixation position is set, the controller 210 controls the fixation optical system so as to project the fixation target onto the set position.

The storage 212 previously stores association information in which multiple fixation positions and sizes of the region for three-dimensional scan are associated. Once a fixation position is set, the controller 210 refers to the association information to specify the size associated with the set fixation position. Further, when carrying out three-dimensional scan, the controller 210 controls the galvano scanner 42 and the OCT unit 100 so as to scan a two-dimensional region with the specified size by the signal light LS.

The fourth process example is explained. In accordance with the site to which line scan is applied, there are cases in which an OCT front image with high resolution is desired and cases in which it is not desired. For example, when observing a cross section of an macula, an OCT front image with higher resolution is desired than the case of observing a cross section of an optic papilla. The present process example automatically changes scan density for three-dimensional scan in accordance with the site to which line scan is applied.

A configuration for realizing the present process example is explained. Similar to the third process example, the ophthalmologic apparatus 1 comprises a fixation optical system. Once a fixation position is set, the controller 210 controls the fixation optical system so as to project the fixation target onto the set position.

The storage 212 previously stores association information in which multiple fixation positions and scan densities for three-dimensional scan are associated. Once a fixation position is set, the controller 210 refers to the association information to specify the scan density associated with the set fixation position. Further, when carrying out three-dimensional scan, the controller 210 controls the galvano scanner 42 and the OCT unit 100 so as to scan a two-dimensional region by the signal light LS with the specified scan density.

The fifth process example is explained. There are cases in which the scan density desired for line scan and the scan density desired for three-dimensional scan are different. For example, there are cases in which line scan is used for observing a cross section of a specific site in detail and three-dimensional scan is used for roughly observing the surrounding thereof. In order to satisfy such a need, the controller 210 may control the galvano scanner 42 and the OCT unit 100 so as to carry out line scan with a first scan density and three-dimensional scan with a second scan density.

[Effects]

The effects of the ophthalmologic apparatus according to the present embodiment are explained.

An ophthalmologic apparatus according to the present embodiment comprises an acquiring part, a first optical system, a forming part, and a controller. The acquiring part is configured to acquire a first front image (the infrared front image 4000, for example) of the fundus of an eye. The acquiring part may be a means that images the fundus such as the retinal camera unit 2, or a means that obtains the first front image from an external apparatus. The first optical system is configured to scan the fundus by signal light and detect interference light of returned light of the signal light from the fundus and reference light. The first optical system includes, for example, the OCT unit 100 and optical elements in the retinal camera unit 2 that form the optical path of the signal light LS. The forming part is configured to repeatedly form both a second front image (the OCT front image 5000, for example) of the fundus and a cross sectional image (the tomographic image 6000, for example) showing a cross section perpendicular to the cross section shown by the second front image based on the detection results repeatedly obtained by the first optical system. The forming part includes, for example, the image forming part 200 and/or the image processor 230. The controller is configured to carry out: a process for displaying the first front image on a display means; a process for displaying, as a moving image, the second front images repeatedly formed by the forming part over the first front image; and a process for displaying, as a moving image, the cross sectional images repeatedly formed by the forming part on the display means. The controller includes, for example, the controller 210.

The ophthalmologic apparatus of the embodiment acquires front images of the fundus by using OCT, wherein the lower limit of the pupil diameter for which OCT is used to image the fundus is smaller than that for a retinal camera. Therefore, it is possible to preferably acquire front images of an eye fundus even though the subject eye is a microcoria eye. It should be noted that the display means may be provided in the ophthalmologic apparatus or may be an external device connected to the ophthalmologic apparatus.

In the embodiment, the first optical system may be configured to alternately execute a first scan mode (three-dimensional scan, for example) in which the irradiation position of the signal light on the fundus is two-dimensionally changed and a second scan mode (line scan or circle scan, for example) in which the irradiation position of the signal light on the fundus is one-dimensionally changed. In this case, the forming part may be configured to carry out: a process that forms the second front images based on the detection results obtained by the first scan mode; and a process that forms the cross sectional images based on the detection results obtained by the second scan mode. Further, the controller may be configured to execute frame update for the movie display of the second front images and frame update for the movie display of the cross sectional images in accordance with the switching between the first and second scan modes of the first optical system. According to such configurations, it is possible to preferably acquire the second front images as a moving image and the tomographic images as a moving image.

In the embodiment, blink detecting part configured to detect the blink of the eye may be provided. In this case, the controller may be configured to stop the frame update of the second front images and/or the frame update of the tomographic images in response to the fact that a blink is detected by the blink detecting part while the first optical system is executing the scan. Further, the controller may be configured to resume the frame update in response to the fact that the blink is no longer detected. According to such configurations, inappropriate frames obtained during blinking are not used for display process. Therefore, it is possible to preferably carry out movie display of the second front images and/or the tomographic images.

In the embodiment, a setting part configured to set a one-dimensional region for the second scan mode may be provided. In this case, the first optical system may be configured to execute the first scan mode (three-dimensional scan) such that a two-dimensional region in which the one-dimensional region set by the setting part is located in the center is scanned by the signal light. According to such configurations, once the line scan position etc. is set for acquiring a tomographic image, the scan area of the second front image that depicts the surrounding of the line scan position etc. is automatically set.

In the embodiment, a fixation optical system may be provided which is configured to project a fixation target onto the fundus based on a preset fixation position. In this case, the first optical system may be configured to execute the first scan mode (three-dimensional scan) such that a two-dimensional region having a size that is associated with the fixation position in advance is scanned by the signal light. According to such configurations, the size of scan area for the second front image is automatically set in accordance with a region of interest of the fundus (that is, in accordance with a fixation position).

In the embodiment, when the fixation optical system is provided, the first optical system may be configured to execute the first scan mode (three-dimensional scan) such that the irradiation position of the signal light is changed at an interval that is associated with the fixation position in advance. According to such configurations, it is possible to carry out OCT measurement for acquiring the second front image with scan density suitable for a region of interest of the fundus.

In the embodiment, the interval of the irradiation positions of the signal light (scan density) in the first scan mode and the interval of the irradiation positions of the signal light (scan density) in the second scan mode may be different. According to such configurations, OCT measurement can be carried out with scan density suitable for the scan mode.

In the embodiment, an information obtaining part configured to obtain information showing the pupil size of the eye, and a second optical system configured to irradiate illumination light on the fundus and repeatedly detect reflected light of the illumination light from the fundus may be provided. In this case, the controller may be configured to switch image display modes based on the information obtained by the information obtaining part. The display modes include, for example, a first display mode in which the second front images are displayed as a movie over the first front image, and a second display mode in which a movie display is carried out based on the detection results repeatedly acquired by the second optical system. According to such configurations, display modes may be automatically selected in accordance with the pupil size of the eye. As a specific example, the first display mode that uses OCT is applied when the eye is a microcoria eye, and the second display mode that uses a retinal camera is applied when the eye is not a microcoria eye.

In the embodiment, the acquiring part may comprise a third optical system configured to irradiate illumination light on the fundus and repeatedly detect reflected light of the illumination light from the fundus. The third optical system is, for example, a retinal camera or SLO. The controller may be configured to display, as the first front image, a moving image based on the detection results repeatedly acquired by the third optical system. According to such configurations, the ophthalmologic apparatus is capable of acquiring, by itself, the first front image that is a moving image.

In the embodiment, an alignment optical system configured to project a target for aligning the first optical system with the eye onto the fundus may be provided. In this case, an image of the target acquired by the third optical system may be displayed together with the first and second front images. According to such configurations, the alignment state of the optical system of the apparatus with respect to the eye can be presented. Moreover, alignment operation can be carried out while observing the first and second front images.

In the embodiment, a focus optical system configured to project, onto the fundus, a target for carrying out focusing of the first optical system on the fundus may be provided. In this case, an image of the target acquired by the third optical system is displayed together with the first and second front images. According to such configurations, the focus state of the optical system of the apparatus with respect to the fundus can be presented. Moreover, focusing operation can be carried out while observing the first and second front images.

Modified Example

The embodiments described above are merely examples. One who intends to implement the present invention may arbitrarily modify (omission, replacement, addition, etc.) within the scope of the invention.

In the above embodiments, the difference in optical path length between the optical path of the signal light LS and the optical path of the reference light LR is changed by changing the position of the optical-path-length changing part 41; however the method for changing the difference in optical path length is not limited to this. For example, it is possible to change the difference in optical path length by providing a reflection mirror (reference mirror) in the optical path of the reference light, and moving this reference mirror along the propagation direction of the reference light to change the optical path length of the reference light. Moreover, it is possible to change the optical path length of the signal light LS by moving the retinal camera unit 2 and/or the OCT unit 100 relative to the eye E, thereby changing the difference in optical path length. Moreover, particularly if the object being measured is not a region of a living body, it is possible to change the difference in optical path length by moving the object being measured in the depth direction (z-direction).

Computer programs for realizing the above embodiments can be stored in any kind of recording medium that can be read by a computer. As this recording medium, for example, a semiconductor memory, an optical disk, a magneto-optic disk (CD-ROM, DVD-RAM, DVD-ROM, MO, and so on), and a magnetic storage (a hard disk, a Floppy Disk™, ZIP, and so on) can be used.

What is claimed is:

1. An ophthalmologic apparatus comprising:
an acquiring part configured to acquire a first front image of the fundus of an eye;
a first optical system configured to scan the fundus by signal light and detect interference light of returned light of the signal light from the fundus and reference light, the first optical system comprising: a light source unit configured to generate the signal light and the reference light and a sensor configured to detect the interference light;
a forming part configured to repeatedly form both a second front image of the fundus and a cross sectional image showing a cross section perpendicular to the cross section shown by the second front image based on the detection results repeatedly obtained by the first optical system; and
a controller configured to display the first front image on a display means, display, as a moving image, the second front images repeatedly formed by the forming part over the first front image, and display, as a moving image, the cross sectional images repeatedly formed by the forming part on the display means.

2. The ophthalmologic apparatus of claim 1, wherein
the first optical system is configured to alternately execute a first scan mode in which the irradiation position of the signal light on the fundus is two-dimensionally changed and a second scan mode in which the irradiation position of the signal light on the fundus is one-dimensionally changed,
the forming part is configured to form the second front images based on the detection results obtained by the first scan mode and form the cross sectional images based on the detection results obtained by the second scan mode, and
the controller is configured to execute frame update for the movie display of the second front images and frame update for the movie display of the cross sectional images in accordance with the switching between the first and second scan modes of the first optical system.

3. The ophthalmologic apparatus of claim 2, further comprising a blink detecting part configured to detect the blink of the eye, wherein
the controller is configured to stop the frame update in response to the fact that a blink is detected by the blink detecting part while the first optical system is executing the scan, and to resume the frame update in response to the fact that the blink is no longer detected.

4. The ophthalmologic apparatus of claim 2, further comprising a setting part configured to set a one-dimensional region for the second scan mode, wherein
the first optical system is configured to execute the first scan mode such that a two-dimensional region in which the one-dimensional region set by the setting part is located in the center is scanned by the signal light.

5. The ophthalmologic apparatus of claim 2, further comprising a fixation optical system configured to project a fixation target onto the fundus based on a preset fixation position, wherein
the first optical system is configured to execute the first scan mode such that a two-dimensional region having a size that is associated with the fixation position in advance is scanned by the signal light.

6. The ophthalmologic apparatus of claim 2, further comprising a fixation optical system configured to project a fixation target onto the fundus based on a preset fixation position, wherein
the first optical system is configured to execute the first scan mode such that the irradiation position of the signal light is changed at an interval that is associated with the fixation position in advance.

7. The ophthalmologic apparatus of claim 2, wherein the interval of the irradiation positions of the signal light in the first scan mode and the interval of the irradiation positions of the signal light in the second scan mode are different.

8. The ophthalmologic apparatus of claim 1, further comprising:
an information obtaining part configured to obtain information showing the pupil size of the eye; and a second optical system configured to irradiate illumination light on the fundus and repeatedly detect reflected light of the illumination light from the fundus, wherein the controller is configured to selectively execute, based on the information obtained by the information obtaining part, a first display mode in which the second front images are displayed as a movie over the first front image, and a second display mode in which a movie display is carried out based on the detection results repeatedly acquired by the second optical system.

9. The ophthalmologic apparatus of claim 1, wherein the acquiring part comprises a third optical system configured to irradiate illumination light on the fundus and repeatedly detect reflected light of the illumination light from the fundus, and the controller is configured to display, as the first front image, a moving image based on the detection results repeatedly acquired by the third optical system.

10. The ophthalmologic apparatus of claim 9, further comprising an alignment optical system configured to project a target for aligning the first optical system with the eye onto the fundus, wherein an image of the target acquired by the third optical system is displayed together with the first and second front images.

11. The ophthalmologic apparatus of claim 9, further comprising a focus optical system configured to project, onto the fundus, a target for carrying out focusing of the first optical system on the fundus, wherein an image of the target acquired by the third optical system is displayed together with the first and second front images.

* * * * *